US006368797B1

(12) United States Patent
Schappert

(10) Patent No.: US 6,368,797 B1
(45) Date of Patent: Apr. 9, 2002

(54) METHODS FOR TREATING OR IDENTIFYING A SUBJECT AT RISK FOR A NEUROLOGICAL DISEASE BY DETERMINING THE PRESENCE OF A VARIANT GPIIIA AND/OR VARIANT BPIIB ALLELE

(75) Inventor: Keith Schappert, Montreal (CA)

(73) Assignee: Variagenics, Inc., Cambridge, MA (US)

( * ) Notice: Subject to any disclaimer, the term of this patent is extended or adjusted under 35 U.S.C. 154(b) by 0 days.

(21) Appl. No.: 09/409,648

(22) Filed: Oct. 1, 1999

Related U.S. Application Data
(60) Provisional application No. 60/102,624, filed on Oct. 1, 1998.

(51) Int. Cl.[7] ................................................ C12Q 1/68
(52) U.S. Cl. ........................................ 435/6; 435/91.2
(58) Field of Search .................................. 435/6, 91.2

(56) References Cited

U.S. PATENT DOCUMENTS

| | | |
|---|---|---|
| 5,391,714 A | 2/1995 | Newman et al. |
| 5,508,167 A | 4/1996 | Roses et al. |
| 5,652,357 A | 7/1997 | Newman et al. |
| 5,716,828 A | 2/1998 | Roses et al. |
| 5,767,248 A | 6/1998 | Roses et al. |
| 5,935,781 A | 8/1999 | Poirier |
| 5,955,266 A | 9/1999 | Bray et al. |

FOREIGN PATENT DOCUMENTS

| | | |
|---|---|---|
| EP | 0200362 | 12/1986 |
| WO | WO 91/08306 | 6/1991 |
| WO | WO 94/09155 | 4/1994 |
| WO | WO 95/29257 | 2/1995 |
| WO | WO 96/02670 | 2/1996 |
| WO | WO 96/03656 | 2/1996 |
| WO | WO 98/27226 | 6/1998 |
| WO | WO 98/27227 | 6/1998 |
| WO | WO 99/14367 | 3/1999 |
| WO | WO 99/15159 | 4/1999 |
| WO | WO 99/66072 | 12/1999 |

OTHER PUBLICATIONS

Skolnick et al., Trends in Biotechnology, 18(1):34–9, Jan. 2000.*
Basani et al., "Glanzmann Thrombasthenia Due to a Two Amino Acid Deletion in the Fourth Calcium–Binding Domain of $\alpha_{IIb}$: Demonstration of the Importance of Calcium–Binding Domains in the conformation of $\alpha_{IIb}\beta_3$," Blood 88:167–173, 1996.
Bray et al. "Physical Linkage of the Genes for Platelet Membrane Glycoproteins IIb and IIIa," Proc. Natl. Acad. Sci. 85:8683–8687, 1988.
Bray et al., "Platelet Glycoprotein IIb. Chromosomal Localization and Tissue Expression," J. Clin, Invest. 80:1812–1817, 1987.
Brindle et al., "Analysis of the Butyrylcholinesterase Gene and nearby Chromosome 3 Markers in Alzheimer Disease," Hum. Mol. Genetics, 7:933–935, 1998.

Cong et al., "Assignment of Human Platelet GP2 (GPIIb) Gene to Chromosome 17, Region q21.1 q21.3," Hum. Genet. 80:389–392, 1988.
Corder et al., "Gene Dose of Apolipoprotein E Type 4 Allele and the Risk of Alzheimer's Disease in Late Onset Families," Science 261:921–923, 1993.
Cummings et al., "Alzheimer's Disease. Etiologies, Pathophysiology, Cognitive Reserve, and Treatment Opportunites," Neurology 51(Supp.1):S2–S17, 1998.
Galasko et al., "Clinical–Neuropathological Correlations in Alzheimer's Disease and Related Dementias," Arch. Neurol. 51:888–895, 1994.
Gustincich et al., "A Fast Method for High–Quality Genomic DNA Extraction from Whole Human Boold," Biotechniques 11:298–300, 1991.
Lyman et al., "Polymorphism of Human Platelet Membrane Glycoprotein IIb Associated with the $Bak^a/Bak^b$ Alloantigen System," Blood 75(12):2343–2348, 1990.
Newman et al., "The Molecular Genetic basis of Glanzmann Thrombasthenia in the Iraqi–Jewish and Arab Populations in Israel," Proc. Natl. Acad. Sci. USA 88:3160–3164, 1991.
Newman et al., "The Human Platelet Alloantigens, $Pl^{A1}$ and $Pl^{A2}$, are Associated with a $Leucine^{33}/Proline^{33}$ Amino Acid Polymorphism in Membrane Glycoprotein IIIa, and are Distinguishable by DNA Typing," J. Clin. Invest. 83:1778–1781, 1989.
Noguchi et al., "Apolipoprotein E Genotype and Alsheimer's Disease," Lancet (letter) 342:737, 1993.
Payami et al., "Apolipoprotein E Genotype and Alsheimer's Disease," Lancet (letter) 342:738, 1993.
Poirier et al., "Apolipoprotein E Phenotype and Alzheimer's Disease," Lancet 342:697–699, 1993.
Poncz et al., "Structure of the Platelet Membrane Glycoprotein IIb," J. Biol. Chem. 262:8476–8482, 1987.
Richard et al., "APOE Genotyping and Response to Drug Treatment in Alzheimer's Disease," Lancet 349:539, 1997.
Singleton et al., "No Association between the K Variant of the Butyrylcholinesterase Gene and Pathologically Confirmed Alzheimer's Disease," Hum. Molecular Genetics 7:937–939, 1998.
Uzan et al., "cDNA Clones for Human Platelet GPIIb Corresponding to mRNA from Megakaryocytes and HEL Cells. Evidence for an Extensive Homology to Other Arg––Gly–Asp Adhesion Receptors," Eur. J. Biochem. 171:87–93, 1988.
Weiss et al., "A Monoclonal Antibody (SZ21) Specific for Platelet GPIIIa Distinguishes $Pl^{A1}$ from $Pl^{A2}$," Tissue Antigens 46:374–381, 1995.
Zimrin et al., "Structure of Platelet Glycoprotein IIIa," J. Clin. Invest. 81:1470–1475, 1988.

* cited by examiner

Primary Examiner—Patrick J. Nolan
(74) Attorney, Agent, or Firm—Clark & Elbing LLP; Kristina Bieker-Brady

(57) ABSTRACT

The invention provides methods for treating or identifying subjects having a neurological disease or at risk for a neurological disease by determining the presence of a variant GPIIIa and/or GPIIb allele.

15 Claims, 8 Drawing Sheets

```
   1 gcgggaggcg gacgagatgc gagcgcggcc gcggccccgg ccgctctggg cgactgtgct
  61 ggcgctgggg gcgctggcgg gcgttggcgt aggagggccc aacatctgta ccacgcgagg
 121 tgtgagctcc tgccagcagt gcctggctgt gagccccatg tgtgcctggt gctctgatga
 181 ggccctgcct ctgggctcac ctcgctgtga cctgaaggag aatctgctga aggataactg
 241 tgccccagaa tccatcgagt tcccagtgag tgaggcccga gtactagagg acaggcccct
 301 cagcgacaag ggctctggag acagctccca ggtcactcaa gtcagtcccc agaggattgc
 361 actccggctc cggccagatg attcgaagaa tttctccatc caagtgcggc aggtggagga
 421 ttaccctgtg gacatctact acttgatgga cctgtcttac tccatgaagg atgatctgtg
 481 gagcatccag aacctgggta ccaagctggc cacccagatg cgaaagctca ccagtaacct
 541 gcggattggc ttcggggcat tgtggacaa gcctgtgtca ccatacatgt atatctcccc
 601 accagaggcc ctcgaaaacc cctgctatga tatgaagacc acctgcttgc ccatgtttgg
 661 ctacaaacac gtgctgacgc taactgacca ggtgacccgc ttcaatgagg aagtgaagaa
 721 gcagagtgtg tcacggaacc gagatgcccc agagggtggc tttgatgcca tcatgcaggc
 781 tacagtctgt gatgaaaaga ttggctggag gaatgatgca tcccacttgc tggtgtttac
 841 cactgatgcc aagactcata tagcattgga cggaaggctg gcaggcattg tccagcctaa
 901 tgacgggcag tgtcatgttg gtagtgacaa tcattactct gcctccacta ccatggatta
 961 tccctctttg gggctgatga ctgagaagct atcccagaaa aacatcaatt gatctttgc
1021 agtgactgaa aatgtagtca atctctatca gaactatagt gagctcatcc cagggaccac
1081 agttggggtt ctgtccatgg attccagcaa tgtcctccag ctcattgttg atgcttatgg
1141 gaaaatccgt tctaaagtag agctggaagt gcgtgacctc cctgaagagt tgtctctatc
1201 cttcaatgcc acctgcctca caatgaggt catccctggc ctcaagtctt gtatgggact
1261 caagattgga gacacggtga gcttcagcat tgaggccaag gtgcgaggct gtccccagga
1321 gaaggagaag tcctttacca taaagcccgt gggcttcaag acagcctga tcgtccaggt
1381 cacctttgat tgtgactgtg cctgccaggc ccaagctgaa cctaatagcc atcgctgcaa
1441 caatggcaat gggacctttg agtgtggggt atgccgttgt gggcctggct ggctgggatc
1501 ccagtgtgag tgctcagagg aggactatcg cccttcccag caggacgaat gcagcccccg
1561 ggagggtcag cccgtctgca gccagcgggg cgagtgcctc tgtggtcaat gtgtctgcca
1621 cagcagtgac tttggcaaga tcacgggcaa gtactgcgag tgtgacgact tctcctgtgt
1681 ccgctacaag ggggagatgt gctcaggcca tggccagtgc agctgtgggg actgcctgtg
1741 tgactccgac tggaccggct actactgcaa ctgtaccacg cgtactgaca cctgcatgtc
1801 cagcaatggg ctgctgtgca gcggccgcgg caagtgtgaa tgtggcagct gtgtctgtat
1861 ccagccgggc tcctatgggg acacctgtga gaagtgcccc acctgcccag atgcctgcac
1921 ctttaagaaa gaatgtgtgg agtgtaagaa gtttgaccgg gagccctaca tgaccgaaaa
1981 tacctgcaac cgttactgcc gtgacgagat tgagtcagtg aaagagctta aggacactgg
2041 caaggatgca gtgaattgta cctataagaa tgaggatgac tgtgtcgtca gattccagta
2101 ctatgaagat tctagtggaa agtccatcct gtatgtggta gaagagccag agtgtcccaa
2161 gggccctgac atcctggtgg tcctgctctc agtgatgggg gccattctgc tcattggcct
2221 tgccgccctg ctcatctgga aactcctcat caccatccac gaccgaaaag aattcgctaa
2281 atttgaggaa gaacgcgcca gagcaaaatg ggacacagcc aacaacccac tgtataaaga
2341 ggccacgtct accttcacca atatcacgta ccggggcact taatgataag cagtcatcct
2401 cagatcatta tcagcctgtg ccacgattgc aggagtccct gccatcatgt ttacagagga
2461 cagtatttgt ggggagggat ttgggggctca gagtgggta ggttgggaga atgtcagtat
2521 gtggaagtgt gggtctgtgt gtgtgtatgt gggggtctgt gtgtttatgt gtgtgtgttg
2581 tgtgtgggag tgtgtaattt aaaattgtga tgtgtcctga taagctgagc tccttagcct
2641 ttgtcccaga atgcctcctg cagggattct tcctgcttag cttgagggtg actatggagc
2701 tgagcaggtg ttcttcatta cctcagtgag aagccagctt tcctcatcag gccattgtcc
2761 ctgaagagaa gggcagggct gaggcctctc attccagagg aagggacacc aagccttggc
2821 tctaccctga gttcataaat ttatggttct caggcctgac tctcagcagc tatggtagga
2881 actgctgggc ttggcagccc gggtcatctg tacctctgcc tcctttcccc tccctcaggc
2941 cgaaggagga gtcagggaga gctgaactat tagagctgcc tgtgccttt gccatcccct
3001 caacccagct atggttctct cgcaagggaa gtccttgcaa gctaattctt tgacctgttg
3061 ggagtgagga tgtctgggcc actcaggggt cattcatggc ctgggggatg taccagcatc
3121 tcccagttca taatcacaac ccttcagatt tgccttattg gcagctctac tctggaggtt
3181 tgtttagaag aagtgtgtca cccttaggcc agcaccatct ctttacctcc taattccaca
```

Fig. 1

```
3241 ccctcactgc tgtagacatt tgctatgagc tggggatgtc tctcatgacc aaatgctttt
3301 cctcaaaggg agagagtgct attgtagagc cagaggtctg gccctatgct tccggcctcc
3361 tgtccctcat ccatagcacc tccacatacc tggccctgag ccttggtgtg ctgtatccat
3421 ccatggggct gattgtattt accttctacc tcttggctgc cttgtgaagg aattattccc
3481 atgagttggc tgggaataag tgccaggatg gaatgatggg tcagttgtat cagcacgtgt
3541 ggcctgttct tctatgggtt ggacaacctc attttaactc agtctttaat ctgagaggcc
3601 acagtgcaat tttattttat ttttctcatg atgaggtttt cttaacttaa aagaacatgt
3661 atataaacat gcttgcatta tatttgtaaa tttatgtgta tggcaaagaa ggagagcata
3721 ggaaaccaca cagacttggg cagggtacag acactcccac ttggcatcat tcacagcaag
3781 tcactggcca gtggctggat ctgtgagggg ctctctcatg atagaaggct atggggatag
3841 atgtgtggac acattggacc tttcctgagg aagagggact gttcttttgt cccagaaaag
3901 cagtggctcc attggtgttg acatacatcc aacattaaaa gccaccccca aatgcccaag
3961 aaaaaaagaa agacttatca acatttgttc catgagg
```

Fig. 1 cont.

```
   1 gcgggaggcg gacgagatgc gagcgcggcc gcggccccgg ccgctctggg cgactgtgct
  61 ggcgctgggg gcgctggcgg gcgttggcgt aggagggccc aacatctgta ccacgcgagg
 121 tgtgagctcc tgccagcagt gcctggctgt gagccccatg tgtgcctggt gctctgatga
 181 ggccctgcct ccg ggctcac tcgctgtga  cctgaaggag aatctgctga aggataactg
 241 tgccccagaa tccatcgagt tcccagtgag tgaggcccga gtactagagg acaggcccct
 301 cagcgacaag ggctctggag acagctccca ggtcactcaa gtcagtcccc agaggattgc
 361 actccggctc cggccagatg attcgaagaa tttctccatc caagtgcggc aggtggagga
 421 ttaccctgtg gacatctact acttgatgga cctgtcttac tccatgaagg atgatctgtg
 481 gagcatccag aacctgggta ccaagctggc cacccagatg cgaaagctca ccagtaacct
 541 gcggattggc ttcgggcat tgtggacaa gcctgtgtca ccatacatgt atatctcccc
 601 accagaggcc ctcgaaaacc cctgctatga tatgaagacc acctgcttgc ccatgtttgg
 661 ctacaaacac gtgctgacgc taactgacca ggtgacccgc ttcaatgagg aagtgaagaa
 721 gcagagtgtg tcacggaacc gagatgcccc agagggtggc tttgatgcca tcatgcaggc
 781 tacagtctgt gatgaaaaga ttggctggag gaatgatgca tcccacttgc tggtgtttac
 841 cactgatgcc aagactcata tagcattgga cggaaggctg gcaggcattg tccagcctaa
 901 tgacgggcag tgtcatgttg gtagtgacaa tcattactct gcctccacta ccatggatta
 961 tccctctttg gggctgatga ctgagaagct atcccagaaa aacatcaatt tgatctttgc
 102 agtgactgaa aatgtagtca atctctatca gaactatagt gagctcatcc cagggaccac
1081 agttggggtt ctgtccatgg attccagcaa tgtcctccag ctcattgttg atgcttatgg
1141 gaaaatccgt tctaaagtag agctggaagt gcgtgacctc cctgaagagt tgtctctatc
1201 cttcaatgcc acctgcctca caatgaggt catccctggc ctcaagtctt gtatgggact
1261 caagattgga gacacggtga gcttcagcat tgaggccaag gtgcgaggct gtccccagga
1321 gaaggagaag tcctttacca taaagcccgt gggcttcaag gacagcctga tcgtccaggt
1381 cacctttgat tgtgactgt cctgccaggc ccaagctgaa cctaatagcc atcgctgcaa
1441 caatggcaat gggaccttg agtgtgggt atgccgttgt gggcctggct ggctgggatc
1501 ccagtgtgag tgctcagagg aggactatcg ccctcccag caggacgaat gcagcccccg
1561 ggagggtcag cccgtctgca gccagcgggg cgagtgcctc tgtggtcaat gtgtctgcca
1621 cagcagtgac tttggcaaga tcacgggcaa gtactgcgag tgtgacgact ctcctgtgt
1681 ccgctacaag ggggagatgt gctcaggcca tggccagtgc agctgtgggg actgcctgtg
1741 tgactccgac tggaccggct actactgcaa ctgtaccacg cgtactgaca cctgcatgtc
1801 cagcaatggg ctgctgtgca gcggccgcgg caagtgtgaa tgtggcagct gtgtctgtat
1861 ccagccgggc tcctatgggg acacctgtga aagtgcccc acctgcccag atgcctgcac
1921 ctttaagaaa gaatgtgtgg agtgtaagaa gtttgaccgg gagccctaca tgaccgaaaa
1981 tacctgcaac cgttactgcc gtgacgagat tgagtcagtg aaagagctta aggacactgg
2041 caaggatgca gtgaattgta cctataagaa tgaggatgac tgtgtcgtca gattccagta
2101 ctatgaagat tctagtggaa agtccatcct gtatgtggta gaagagccag agtgtcccaa
2161 gggccctgac atcctggtgg tcctgctctc agtgatggg gccattctgc tcattggcct
2221 tgccgccctg ctcatctgga aactcctcat caccatccac gaccgaaaag aattcgctaa
2281 atttgaggaa gaacgcgcca gagcaaaatg ggacacagcc aacaacccac tgtataaaga
2341 ggccacgtct accttcacca atatcacgta ccggggcact aatgataag cagtcatcct
2401 cagatcatta tcagcctgtg ccacgattgc aggagtccct gccatcatgt ttacagagga
2461 cagtatttgt ggggagggat ttggggctca gagtggggta ggttgggaga atgtcagtat
2521 gtggaagtgt gggtctgtgt gtgtgtatgt ggggtctgt gtgtttatgt gtgtgtgttg
2581 tgtgtgggag tgtgtaattt aaaattgtga tgtgtcctga taagctgagc tccttagcct
2641 ttgtcccaga atgcctcctg cagggattct tcctgcttag cttgagggtg actatggagc
2701 tgagcaggtg ttcttcatta cctcagtgag aagccagctt tcctcatcag gccattgtcc
2761 ctgaagagaa gggcagggct gaggcctctc attccagagg aagggacacc aagccttggc
2821 tctaccctga gttcataaat ttatggttct caggcctgac tctcagcagc tatggtagga
2881 actgctgggc ttggcagccc gggtcatctg tacctctgcc tcctttcccc tccctcaggc
2941 cgaaggagga gtcaggaga gctgaactat tagagctgcc tgtgccttt gccatcccct
3001 caacccagct atggttctct cgcaaggaa gtccttgcaa gctaattctt tgacctgttg
3061 ggagtgagga tgtctgggcc actcagggt cattcatggc ctggggatg taccagcatc
3121 tcccagttca taatcacaac ccttcagatt tgccttattg gcagctctac tctggaggtt
3181 tgtttagaag aagtgtgtca cccttaggcc agcaccatct ctttacctcc taattccaca
```

Fig. 2

```
3241 ccctcactgc tgtagacatt tgctatgagc tgggatgtc tctcatgacc aaatgctttt
3301 cctcaaaggg agagagtgct attgtagagc cagaggtctg gccctatgct tccggcctcc
3361 tgtccctcat ccatagcacc tccacatacc tggccctgag ccttggtgtg ctgtatccat
3421 ccatggggct gattgtattt accttctacc tcttggctgc cttgtgaagg aattattccc
3481 atgagttggc tgggaataag tgccaggatg gaatgatggg tcagttgtat cagcacgtgt
3541 ggcctgttct tctatgggtt ggacaacctc attttaactc agtctttaat ctgagaggcc
3601 acagtgcaat tttattttat ttttctcatg atgaggtttt cttaacttaa aagaacatgt
3661 atataaacat gcttgcatta tatttgtaaa tttatgtgta tggcaaagaa ggagagcata
3721 ggaaaccaca cagacttggg cagggtacag acactcccac ttggcatcat tcacagcaag
3781 tcactggcca gtggctggat ctgtgagggg ctctctcatg atagaaggct atggggatag
3841 atgtgtggac acattggacc tttcctgagg aagagggact gttcttttgt cccagaaaag
3901 cagtggctcc attggtgttg acatacatcc aacattaaaa gccaccccca aatgcccaag
3961 aaaaaaagaa agacttatca acatttgttc catgagg
```

Fig. 2 cont.

```
  1 MRARPRPRPL WVTVLALGAL AGVGVGGPNI CTTRGVSSCQ QCLAVSPMCA WCSDEALPLG  60
 61 SPRCDLKENL LKDNCAPESI EFPVSEARVL EDRPLSDKGS GDSSQVTQVS PQRIALRLRP 120
121 DDSKNFSIQV RQVEDYPVDI YYLMDLSYSM KDDLWSIQNL GTKLATQMRK LTSNLRIGFG 180
181 AFVDKPVSPY MYISPPEALE NPCYDMKTTC LPMFGYKHVL TLTDQVTRFN EEVKKQSVSR 240
241 NRDAPEGGFD AIMQATVCDE KIGWRNDASH LLVFTTDAKT HIALDGRLAG IVQPNDGQCH 300
301 VGSDNHYSAS TTMDYPSLGL MTEKLSQKNI NLIFAVTENV VNLYQNYSEL IPGTTVGVLS 360
361 MDSSNVLQLI VDAYGKIRSK VELEVRDLPE ELSLSFNATC LNNEVIPGLK SCMGLKIGDT 420
421 VSFSIEAKVR GCPQEKEKSF TIKPVGFKDS LIVQVTFDCD CACQAQAEPN SHRCNNGNGT 480
481 FECGVCRCGP GWLGSQCECS EEDYRPSQQD ECSPREGQPV CSQRGECLCG QCVCHSSDFG 540
541 KITGKYCECD DFSCVRYKGE MCSGHGQCSC GDCLCDSDWT GYYCNCTTRT DTCMSSNGLL 600
601 CSGRGKCECG SCVCIQPGSY GDTCEKCPTC PDACTFKKEC VECKKFDREP YMTENTCNRY 660
661 CRDEIESVKE LKDTGKDAVN CTYKNEDDCV VRFQYYEDSS GKSILYVVEE PECPKGPDIL 720
721 VVLLSVMGAI LLIGLAALLI WKLLITIHDR KEFAKFEEER ARAKWDTANN PLYKEATSTF 780
781 TNITYRGT
```

Fig. 3

```
  1 MRARPRPRPL WVTVLALGAL AGVGVGGPNI CTTRGVSSCQ QCLAVSPMCA WCSDEALPPG  60
 61 SPRCDLKENL LKDNCAPESI EFPVSEARVL EDRPLSDKGS GDSSQVTQVS PQRIALRLRP 120
121 DDSKNFSIQV RQVEDYPVDI YYLMDLSYSM KDDLWSIQNL GTKLATQMRK LTSNLRIGFG 180
181 AFVDKPVSPY MYISPPEALE NPCYDMKTTC LPMFGYKHVL TLTDQVTRFN EEVKKQSVSR 240
241 NRDAPEGGFD AIMQATVCDE KIGWRNDASH LLVFTTDAKT HIALDGRLAG IVQPNDGQCH 300
301 VGSDNHYSAS TTMDYPSLGL MTEKLSQKNI NLIFAVTENV VNLYQNYSEL IPGTTVGVLS 360
361 MDSSNVLQLI VDAYGKIRSK VELEVRDLPE ELSLSFNATC LNNEVIPGLK SCMGLKIGDT 420
421 VSFSIEAKVR GCPQEKEKSF TIKPVGFKDS LIVQVTFDCD CACQAQAEPN SHRCNNGNGT 480
481 FECGVCRCGP GWLGSQCECS EEDYRPSQQD ECSPREGQPV CSQRGECLCG QCVCHSSDFG 540
541 KITGKYCECD DFSCVRYKGE MCSGHGQCSC GDCLCDSDWT GYYCNCTTRT DTCMSSNGLL 600
601 CSGRGKCECG SCVCIQPGSY GDTCEKCPTC PDACTFKKEC VECKKFDREP YMTENTCNRY 660
661 CRDEIESVKE LKDTGKDAVN CTYKNEDDCV VRFQYYEDSS GKSILYVVEE PECPKGPDIL 720
721 VVLLSVMGAI LLIGLAALLI WKLLITIHDR KEFAKFEEER ARAKWDTANN PLYKEATSTF 780
781 TNITYRGT
```

Fig. 4

```
   1 gatggccaga gctttgtgtc cactgcaagc cctctggctt ctggagtggg tgctgctgct
  61 cttgggacct tgtgctgccc ctccagcctg ggccttgaac ctggacccag tgcagctcac
 121 cttctatgca ggccccaatg gcagccagtt tggattttca ctggacttcc acaaggacag
 181 ccatgggaga gtggccatcg tggtgggcgc cccgcggacc ctgggcccca gccaggagga
 241 gacgggcggc gtgttcctgt gccctggag ggccgaggc ggccagtgcc cctcgctgct
 301 ctttgacctc cgtgatgaga cccgaaatgt aggctcccaa actttacaaa ccttcaaggc
 361 ccgccaagga ctgggggcgt cggtcgtcag ctggagcgac gtcattgtgg cctgcgcccc
 421 ctgcagcac tggaacgtcc tagaaaagac tgaggaggct gagaagacgc ccgtaggtag
 481 ctgcttttg gctcagccag agagcggccg ccgcgccgag tactcccct gtcgcgggaa
 541 caccctgagc cgcatttacg tggaaaatga ttttagctgg acaagcgtt actgtgaagc
 601 gggcttcagc tccgtggtca ctcaggccgg agagctggtg cttggggctc ctggcggcta
 661 ttatttctta ggtctcctgg cccaggctcc agttgcggat atttctcga gttaccgccc
 721 aggcatcctt ttgtggcacg tgtcctccca gagcctctcc tttgactcca gcaacccaga
 781 gtacttcgac ggctactggg ggtactcggt ggccgtgggc gagttcgacg gggatctcaa
 841 cactacagaa tatgtcgtcg gtgccccac ttggagctgg accctgggag cggtggaaat
 901 tttggattcc tactaccaga ggctgcatcg gctgcgcgca gagcagatgg cgtcgtattt
 961 tgggcattca gtggctgtca ctgacgtcaa cggggatggg aagcatgatc tgctggtggg
1021 cgctccactg tatatggaga ccgggcaga ccgaaaactg gccgaagtgg ggcgtgtgta
1081 tttgttcctg cagccgcgag gcccccacgc gctgggtgcc cccagcctcc tgctgactgg
1141 cacacagctc tatgggcgat tcggctctgc catcgcaccc ctgggcgacc tcgaccggga
1201 tggctacaat gacattgcag tgctgccccc ctacgggggt cccagtggcc ggggccaagt
1261 gctggtgttc ctgggtcaga gtgaggggct gaggtcacgt ccctcccagg tcctggacag
1321 cccttcccc acaggctctg cctttggctt ctcccttcga ggtgccgtag acatcgatga
1381 caacggatac ccagacctga tcgtgggagc ttacggggcc aaccaggtgg ctgtgtacag
1441 agctcagcca gtggtgaagg cctctgtcca gctactggtg caagattcac tgaatcctgc
1501 tgtgaagagc tgtgtcctac ctcagaccaa gacacccgtg agctgcttca acatccagat
1561 gtgtgttgga gccactgggc acaacattcc tcagaagcta tccctaaatg ccgagctgca
1621 gctggaccgg cagaagcccc gccagggccg gcgggtgctg ctgctgggct ctcaacaggc
1681 aggcaccacc ctgaacctgg atctgggcgg aaagcacagc cccatctgcc acaccaccat
1741 ggccttcctt cgagatgagg cagacttccg ggacaagctg agccccattg tgctcagcct
1801 caatgtgtcc ctaccgccca cggaggctgg aatggcccct gctgtcgtgc tgcatggaga
1861 cacccatgtg caggagcaga cacgaatcgt cctggactct ggggaagatg acgtatgtgt
1921 gccccagctt cagctcactg ccagcgtgac gggctccccg ctcctagttg gggcagataa
1981 tgtcctggag ctgcagatgg acgcagccaa cgagggcgag ggggcctatg aagcagagct
2041 ggccgtgcac ctgccccagg gcgcccacta catgcgggcc ctaagcaatg tcgagggctt
2101 tgagagactc atctgtaatc agaagaagga gaatgagacc agggtggtgc tgtgtgagct
2161 gggcaacccc atgaagaaga acgcccagat aggaatcgcg atgttggtga gcgtggggaa
2221 tctggaagag gctggggagt ctgtgtcctt ccagctgcag atacggagca agaacagcca
2281 gaatccaaac agcaagattg tgctgctgga cgtgccggtc cgggcagagg cccaagtgga
2341 gctgcgaggg aactcctttc cagcctccct ggtggtggca gcagaagaag gtgagaggga
2401 gcagaacagc ttggacagct ggggacccaa agtggagcac acctatgagc tccacaacaa
2461 tggccctggg actgtgaatg gtcttcacct cagcatccac cttccgggac agtcccagcc
2521 ctccgacctg ctctacatcc tggatataca gccccagggg ggccttcagt gcttcccaca
2581 gcctcctgtc aaccctctca aggtggactg ggggctgccc atc cccagcc cctccccat
2641 tcacccggcc catcacaagc gggatcgcag acagatcttc ctgccagagc ccgagcagcc
2701 ctcgaggctt caggatccag ttctcgtaag ctgcgactcg gcgccctgta ctgtggtgca
2761 gtgtgacctg caggagatgg cgcgcgggca gcgggccatg gtcacggtgc tggccttcct
2821 gtggctgccc agcctctacc agaggcctct ggatcagttt gtgctgcagt cgcacgcatg
2881 gttcaacgtg tcctccctcc cctatgcggt gccccgctc agcctgcccc gaggggaagc
2941 tcaggtgtgg acacagctgc tccgggcctt ggaggagagg gccattccaa tctggtgggt
3001 gctggtgggt gtgctgggtg gcctgctgct gctcaccatc ctggtcctgg ccatgtggaa
3061 ggtcggcttc ttcaagcgga accggccacc cctggaagaa gatgatgaag aggggagtg
3121 atggtgcagc ctacactatt ctagcaggag ggttgggcgt gctacctgca ccgccccttc
3181 tccaacaagt tgcctccaag ctttgggttg agctgttcc attgggtcct cttggtgtcg
3241 tttccctccc aacagagctg ggctaccccc ctcctgctg cctaataaag agactgagcc
3301 ctg
```

Fig. 5

```
   1 gatggccaga gctttgtgtc cactgcaagc cctctggctt ctggagtggg tgctgctgct
  61 cttgggacct tgtgctgccc ctccagcctg ggccttgaac ctggacccag tgcagctcac
 121 cttctatgca ggccccaatg gcagccagtt tggattttca ctggacttcc acaaggacag
 181 ccatgggaga gtggccatcg tggtgggcgc cccgcggacc ctgggcccca gccaggagga
 241 gacgggcggc gtgttcctgt gcccctggag ggccgagggc ggccagtgcc cctcgctgct
 301 ctttgacctc cgtgatgaga cccgaaatgt aggctcccaa actttacaaa ccttcaaggc
 361 ccgccaagga ctgggggcgt cggtcgtcag ctggagcgac gtcattgtgg cctgcgcccc
 421 ctggcagcac tggaacgtcc tagaaaagac tgaggaggct gagaagacgc ccgtaggtag
 481 ctgcttttg gctcagccag agagcggccg ccgcgccgag tactccccct gtcgcgggaa
 541 caccctgagc cgcatttacg tggaaaatga ttttagctgg acaagcgtt actgtgaagc
 601 gggcttcagc tccgtggtca ctcaggccgg agagctggtg cttggggctc ctggcggcta
 661 ttatttctta ggtctcctgg cccaggctcc agttgcggat attttctcga gttaccgccc
 721 aggcatcctt ttgtggcacg tgtcctccca gagcctctcc tttgactcca gcaacccaga
 781 gtacttcgac ggctactggg ggtactcggt ggccgtgggc gagttcgacg gggatctcaa
 841 cactacagaa tatgtcgtcg gtgccccac ttggagctgg accctgggag cggtggaaat
 901 tttggattcc tactaccaga ggctgcatcg gctgcgcgca gagcagatgg cgtcgtattt
 961 tgggcattca gtggctgtca ctgacgtcaa cggggatggg aggcatgatc tgctggtggg
1021 cgctccactg tatatggaga gccgggcaga ccgaaaactg gccgaagtgg ggcgtgtgta
1081 tttgttcctg cagccgcgag gccccacgc gctgggtgcc cccagcctcc tgctgactgg
1141 cacacagctc tatgggcgat tcggctctgc catcgcaccc ctgggcgacc tcgaccggga
1201 tggctacaat gacattgcag tggctgcccc ctacggggt cccagtggcc ggggccaagt
1261 gctggtgttc ctgggtcaga gtgaggggct gaggtcacgt ccctcccagg tcctggacag
1321 ccccttcccc acaggctctg cctttggctt ctcccttcga ggtgccgtag acatcgatga
1381 caacggatac ccagacctga tcgtgggagc ttacggggcc aaccaggtgg ctgtgtacag
1441 agctcagcca gtggtgaagg cctctgtcca gctactggtg caagattcac tgaatcctgc
1501 tgtgaagagc tgtgtcctac ctcagaccaa gacacccgtg agctgcttca catccagat
1561 gtgtgttgga gccactgggc acaacattcc tcagaagcta tccctaaatg ccgagctgca
1621 gctggaccgg cagaagcccc gccagggccg gcgggtgctg ctgctgggct tcaacaggc
1681 aggcaccacc ctgaacctgg atctgggcgg aaagcacagc cccatctgcc acaccaccat
1741 ggccttcctt cgagatgagg cagacttccg ggacaagctg agccccattg tgctcagcct
1801 caatgtgtcc ctaccgccca cggaggctgg aatggcccct gctgtcgtgc tgcatggaga
1861 cacccatgtg caggagcaga cacgaatcgt cctggactct ggggaagatg acgtatgtgt
1921 gccccagctt cagctcactg ccagcgtgac gggctccccg ctcctagttg gggcagataa
1981 tgtcctggag ctgcagatgg acgcagccaa cgagggcgag ggggcctatg aagcagagct
2041 ggccgtgcac ctgccccagg cgcccactα catgcgggcc ctaagcaatg tcgagggctt
2101 tgagagactc atctgtaatc agaagaagga gaatgagacc agggtggtgc tgtgtgagct
2161 gggcaacccc atgaagaaga acgcccagat aggaatcgcg atgttggtga gcgtggggaa
2221 tctggaagag gctggggagt ctgtgtcctt ccagctgcag atacggagca agaacagcca
2281 gaatccaaac agcaagattg tgctgctgga cgtgccggtc cgggcagagg cccaagtgga
2341 gctgcgaggg aactcctttc agcctccct ggtggtggca gcagaagaag gtgagaggga
2401 gcagaacagc ttggacagct ggggacccaa agtggagcac acctatgagc tccacaacaa
2461 tggccctggg actgtgaatg gtcttcacct cagcatccac cttccgggac agtcccagcc
2521 ctccgacctg ctctacatcc tggatataca gccccagggg ggccttcagt gcttcccaca
2581 gcctcctgtc aaccctctca aggtggactg ggggctgccc agc cccagcc cctccccat
2641 tcacccggcc catcacaagc gggatcgcag acagatcttc ctgccagagc ccgagcagcc
2701 ctcgaggctt caggatccag ttctcgtaag ctgcgactcg gcgccctgta ctgtggtgca
2761 gtgtgacctg caggagatgg cgcgcgggca gcgggccatg gtcacggtgc tggccttcct
2821 gtggctgccc agcctctacc agaggcctct ggatcagttt gtgctgcagt cgcacgcatg
2881 gttcaacgtg tcctccctcc cctatgcggt gccccgctc agcctgcccc gagggggaagc
2941 tcaggtgtgg acacagctgc tccgggcctt ggaggagagg gccattccaa tctggtgggt
3001 gctggtgggt gtgctgggtg gcctgctgct gctcaccatc ctggtcctgg ccatgtggaa
3061 ggtcgcttc ttcaagcgga accggccacc cctggaagaa gatgatgaag agggggagtg
3121 atggtgcagc ctacactatt ctagcaggag ggttgggcgt gctacctgca ccgcccttc
3181 tccaacaagt gcctccaag ctttgggttg gagctgttcc attgggtcct cttggtgtcg
3241 tttccctccc aacagagctg ggctacccc cctcctgctg cctaataaag agactgagcc
3301 ctg
```

Fig. 6

MARALCPLQALWLLEWVLLLLGPCAAPPAWALNLDPVQLTFYAGPNGSQFGFSLDFHKDSHGRVAIVVGAPR
TLGPSQEETGGVFLCPWRAEGGQCPSLLFDLRDETRNVGSQTLQTFKARQGLGASVVSWSDVIVACAPWQHW
NVLEKTEEAEKTPVGSCFLAQPESGRRAEYSPCRGNTLSRIYVENDFSWDKRYCEAGFSSVVTQAGELVLGA
PGGYYFLGLLAQAPVADIFSSYRPGILLWHVSSQSLSFDSSNPEYFDGYWGYSVAVGEFDGDLNTTEYVVGA
PTWSWTLGAVEILDSYYQRLHRLRAEQMASYFGHSVAVTDVNGDGRHDLLVGAPLYMESRADRKLAEVGRVY
LFLQPRGPHALGAPSLLLTGTQLYGRFGSAIAPLGDLDRDGYNDIAVAAPYGGPSGRGQVLVFLGQSEGLRS
RPSQVLDSPFPTGSAFGFSLRGAVDIDDNGYPDLIVGAYGANQVAVYRAQPVVKASVQLLVQDSLNPAVKSC
VLPQTKTPVSCFNIQMCVGATGHNIPQKLSLNAELQLDRQKPRQGRRVLLLGSQQAGTTLNLDLGGKHSPIC
HTTMAFLRDEADFRDKLSPIVLSLNVSLPPTEAGMAPAVVLHGDTHVQEQTRIVLDSGEDDVCVPQLQLTAS
VTGSPLLVGADNVLELQMDAANEGEGAYEAELAVHLPQGAHYMRALSNVEGFERLICNQKKENETRVVLCEL
GNPMKKNAQIGIAMLVSVGNLEEAGESVSFQLQIRSKNSQNPNSKIVLLDVPVRAEAQVELRGNSFPASLVV
AAEEGEREQNSLDSWGPKVEHTYELHNNGPGTVNGLHLSIHLPGQSQPSDLLYILDIQPQGGLQCFPQPPVN
PLKVDWGLPIPSPSPIHPAHHKRDRRQIFLPEPEQPSRLQDPVLVSCDSAPCTVVQCDLQEMARGQRAMV
TVLAFLWLPSLYQRPLDQFVLQSHAWFNVSSLPYAVPPLSLPRGEAQVWTQLLRALEERAIPIWWVLVGVLG
GLLLLTILVLAMWKVGFFKRNRPPLEEDDEEGE

Fig. 7

MARALCPLQALWLLEWVLLLLGPCAAPPAWALNLDPVQLTFYAGPNGSQFGFSLDFHKDSHGRVAIVVGAPR
TLGPSQEETGGVFLCPWRAEGGQCPSLLFDLRDETRNVGSQTLQTFKARQGLGASVVSWSDVIVACAPWQHW
NVLEKTEEAEKTPVGSCFLAQPESGRRAEYSPCRGNTLSRIYVENDFSWDKRYCEAGFSSVVTQAGELVLGA
PGGYYFLGLLAQAPVADIFSSYRPGILLWHVSSQSLSFDSSNPEYFDGYWGYSVAVGEFDGDLNTTEYVVGA
PTWSWTLGAVEILDSYYQRLHRLRAEQMASYFGHSVAVTDVNGDGRHDLLVGAPLYMESRADRKLAEVGRVY
LFLQPRGPHALGAPSLLLTGTQLYGRFGSAIAPLGDLDRDGYNDIAVAAPYGGPSGRGQVLVFLGQSEGLRS
RPSQVLDSPFPTGSAFGFSLRGAVDIDDNGYPDLIVGAYGANQVAVYRAQPVVKASVQLLVQDSLNPAVKSC
VLPQTKTPVSCFNIQMCVGATGHNIPQKLSLNAELQLDRQKPRQGRRVLLLGSQQAGTTLNLDLGGKHSPIC
HTTMAFLRDEADFRDKLSPIVLSLNVSLPPTEAGMAPAVVLHGDTHVQEQTRIVLDSGEDDVCVPQLQLTAS
VTGSPLLVGADNVLELQMDAANEGEGAYEAELAVHLPQGAHYMRALSNVEGFERLICNQKKENETRVVLCEL
GNPMKKNAQIGIAMLVSVGNLEEAGESVSFQLQIRSKNSQNPNSKIVLLDVPVRAEAQVELRGNSFPASLVV
AAEEGEREQNSLDSWGPKVEHTYELHNNGPGTVNGLHLSIHLPGQSQPSDLLYILDIQPQGGLQCFPQPPVN
PLKVDWGLPSPSPSPIHPAHHKRDRRQIFLPEPEQPSRLQDPVLVSCDSAPCTVVQCDLQEMARGQRAMV
TVLAFLWLPSLYQRPLDQFVLQSHAWFNVSSLPYAVPPLSLPRGEAQVWTQLLRALEERAIPIWWVLVGVLG
GLLLLTILVLAMWKVGFFKRNRPPLEEDDEEGE

Fig. 8

United States Patent US 6,368,797 B1

SEQUENCE LISTING

<160> NUMBER OF SEQ ID NOS: 14

<210> SEQ ID NO 1
<211> LENGTH: 3997
<212> TYPE: DNA
<213> ORGANISM: Homo sapiens

<400> SEQUENCE: 1

| | | | | | | |
|---|---|---|---|---|---|---|
| gcgggaggcg | gacgagatgc | gagcgcggcc | gcggccccgg | ccgctctggg | cgactgtgct | 60 |
| ggcgctgggg | gcgctggcgg | gcgttggcgt | aggagggccc | aacatctgta | ccacgcgagg | 120 |
| tgtgagctcc | tgccagcagt | gcctggctgt | gagccccatg | tgtgcctggt | gctctgatga | 180 |
| ggccctgcct | ctgggctcac | ctcgctgtga | cctgaaggag | aatctgctga | aggataactg | 240 |
| tgccccagaa | tccatcgagt | tcccagtgag | tgaggcccga | gtactagagg | acaggcccct | 300 |
| cagcgacaag | ggctctggag | acagctccca | ggtcactcaa | gtcagtcccc | agaggattgc | 360 |
| actccggctc | cggccagatg | attcgaagaa | tttctccatc | caagtgcggc | aggtggagga | 420 |
| ttaccctgtg | gacatctact | acttgatgga | cctgtcttac | tccatgaagg | atgatctgtg | 480 |
| gagcatccag | aacctgggta | ccaagctggc | cacccagatg | cgaaagctca | ccagtaacct | 540 |
| gcggattggc | ttcgggggcat | ttgtggacaa | gcctgtgtca | ccatacatgt | atatctcccc | 600 |
| accagaggcc | ctcgaaaacc | cctgctatga | tatgaagacc | acctgcttgc | ccatgtttgg | 660 |
| ctacaaacac | gtgctgacgc | taactgacca | ggtgacccgc | ttcaatgagg | aagtgaagaa | 720 |
| gcagagtgtg | tcacggaacc | gagatgcccc | agagggtggc | tttgatgcca | tcatgcaggc | 780 |
| tacagtctgt | gatgaaaaga | ttggctggag | gaatgatgca | tcccacttgc | tggtgtttac | 840 |
| cactgatgcc | aagactcata | tagcattgga | cggaaggctg | gcaggcattg | tccagcctaa | 900 |
| tgacgggcag | tgtcatgttg | gtagtgacaa | tcattactct | gcctccacta | ccatggatta | 960 |
| tccctctttg | gggctgatga | ctgagaagct | atcccagaaa | aacatcaatt | tgatctttgc | 1020 |
| agtgactgaa | aatgtagtca | atctctatca | gaactatagt | gagctcatcc | cagggaccac | 1080 |
| agttgggggtt | ctgtccatgg | attccagcaa | tgtcctccag | ctcattgttg | atgcttatgg | 1140 |
| gaaaatccgt | tctaaagtag | agctggaagt | gcgtgacctc | cctgaagagt | tgtctctatc | 1200 |

-continued

```
cttcaatgcc acctgcctca acaatgaggt catccctggc tcaagtctt gtatgggact    1260
caagattgga gacacggtga gcttcagcat tgaggccaag gtgcgaggct gtccccagga    1320
gaaggagaag tcctttacca taaagcccgt gggcttcaag acagcctga tcgtccaggt    1380
cacctttgat tgtgactgtg cctgccaggc ccaagctgaa cctaatagcc atcgctgcaa    1440
caatggcaat gggacctttg agtgtggggt atgccgttgt gggcctggct ggctgggatc    1500
ccagtgtgag tgctcagagg aggactatcg cccttcccag caggacgaat gcagccccg    1560
ggagggtcag cccgtctgca gccagcgggg cgagtgcctc tgtggtcaat gtgtctgcca    1620
cagcagtgac tttggcaaga tcacgggcaa gtactgcgag tgtgacgact tctcctgtgt    1680
ccgctacaag ggggagatgt gctcaggcca tggccagtgc agctgtgggg actgcctgtg    1740
tgactccgac tggaccggct actactgcaa ctgtaccacg cgtactgaca cctgcatgtc    1800
cagcaatggg ctgctgtgca gcggccgcgg caagtgtgaa tgtggcagct gtgtctgtat    1860
ccagccgggc tcctatgggg acacctgtga aagtgcccc acctgcccag atgcctgcac    1920
ctttaagaaa gaatgtgtgg agtgtaagaa gtttgaccgg gagccctaca tgaccgaaaa    1980
tacctgcaac cgttactgcc gtgacgagat tgagtcagtg aaagagctta aggacactgg    2040
caaggatgca gtgaattgta cctataagaa tgaggatgac tgtgtcgtca gattccagta    2100
ctatgaagat tctagtggaa agtccatcct gtatgtggta aagagccag agtgtcccaa    2160
gggccctgac atcctggtgg tcctgctctc agtgatgggg gccattctgc tcattggcct    2220
tgccgccctg ctcatctgga aactcctcat caccatccac gaccgaaaag aattcgctaa    2280
atttgaggaa gaacgcgcca gagcaaaatg ggacacagcc aacaacccac tgtataaaga    2340
ggccacgtct accttcacca atatcacgta ccggggcact aatgataag cagtcatcct    2400
cagatcatta tcagcctgtg ccacgattgc aggagtccct gccatcatgt ttacagagga    2460
cagtatttgt ggggagggat tggggctca gagtgggta ggttgggaga atgtcagtat    2520
gtggaagtgt gggtctgtgt gtgtgtatgt gggggtctgt gtgtttatgt gtgtgtgttg    2580
tgtgtgggag tgtgtaattt aaaattgtga tgtgtcctga taagctgagc tccttagcct    2640
ttgtcccaga atgcctcctg caggggattct tcctgcttag cttgagggtg actatggagc    2700
tgagcaggtg ttcttcatta cctcagtgag aagccagctt tcctcatcag gccattgtcc    2760
ctgaagagaa gggcagggct gaggcctctc attccagagg aagggacacc aagccttggc    2820
tctaccctga gttcataaat ttatggttct caggcctgac tctcagcagc tatggtagga    2880
actgctgggc ttggcagccc gggtcatctg tacctctgcc tcctttcccc tccctcaggc    2940
cgaaggagga gtcagggaga gctgaactat tagagctgcc tgtgcctttt gccatcccct    3000
caacccagct atggttctct cgcaagggaa gtccttgcaa gctaattctt tgacctgttg    3060
ggagtgagga tgtctgggcc actcaggggt cattcatggc ctgggggatg taccagcatc    3120
tcccagttca taatcacaac ccttcagatt tgccttattg gcagctctac tctggaggtt    3180
tgtttagaag aagtgtgtca cccttaggcc agcaccatct cttttacctcc taattccaca    3240
ccctcactgc tgtagacatt tgctatgagc tgggatgtc tctcatgacc aaatgctttt    3300
cctcaaaggg agagagtgct attgtagagc cagaggtctg gccctatgct tccggcctcc    3360
tgtccctcat ccatagcacc tccacatacc tggccctgag ccttggtgtg ctgtatccat    3420
ccatggggct gattgtattt accttctacc tcttggctgc cttgtgaagg aattattccc    3480
atgagttggc tgggaataag tgccaggatg gaatgatggg tcagttgtat cagcacgtgt    3540
ggcctgttct tctatgggtt ggacaacctc attttaactc agtctttaat ctgagaggcc    3600
```

| | |
|---|---:|
| acagtgcaat tttattttat ttttctcatg atgaggtttt cttaacttaa aagaacatgt | 3660 |
| atataaacat gcttgcatta tatttgtaaa tttatgtgta tggcaaagaa ggagagcata | 3720 |
| ggaaaccaca cagacttggg cagggtacag acactcccac ttggcatcat tcacagcaag | 3780 |
| tcactggcca gtggctggat ctgtgagggg ctctctcatg atagaaggct atgggdatag | 3840 |
| atgtgtggac acattggacc tttcctgagg aagagggact gttcttttgt cccagaaaag | 3900 |
| cagtggctcc attggtgttg acatacatcc aacattaaaa gccaccccca aatgcccaag | 3960 |
| aaaaaaagaa agacttatca acatttgttc catgagg | 3997 |

<210> SEQ ID NO 2
<211> LENGTH: 3997
<212> TYPE: DNA
<213> ORGANISM: Homo sapiens

<400> SEQUENCE: 2

| | |
|---|---:|
| gcgggaggcg acgagatgc gagcgcggcc gcggccccgg ccgctctggg cgactgtgct | 60 |
| ggcgctgggg gcgctggcgg gcgttggcgt aggagggccc aacatctgta ccacgcgagg | 120 |
| tgtgagctcc tgccagcagt gcctggctgt gagccccatg tgtgcctggt gctctgatga | 180 |
| ggccctgcct ccgggctcac ctcgctgtga cctgaaggag aatctgctga aggataactg | 240 |
| tgccccagaa tccatcgagt tcccagtgag tgaggcccga gtactagagg acaggcccct | 300 |
| cagcgacaag ggctctggag acagctccca ggtcactcaa gtcagtcccc agaggattgc | 360 |
| actccggctc cggccagatg attcgaagaa tttctccatc caagtgcggc aggtggagga | 420 |
| ttaccctgtg gacatctact acttgatgga cctgtcttac tccatgaagg atgatctgtg | 480 |
| gagcatccag aacctgggta ccaagctggc cacccagatg cgaaagctca ccagtaacct | 540 |
| gcggattggc ttcgggggcat tgtggacaa gcctgtgtca ccatacatgt atatctcccc | 600 |
| accagaggcc ctcgaaaacc cctgctatga tatgaagacc acctgcttgc ccatgtttgg | 660 |
| ctacaaacac gtgctgacgc taactgacca ggtgacccgc ttcaatgagg aagtgaagaa | 720 |
| gcagagtgtg tcacggaacc gagatgcccc agagggtggc tttgatgcca tcatgcaggc | 780 |
| tacagtctgt gatgaaaaga ttggctggag gaatgatgca tcccacttgc tggtgtttac | 840 |
| cactgatgcc aagactcata tagcattgga cggaaggctg gcaggcattg tccagcctaa | 900 |
| tgacgggcag tgtcatgttg gtagtgacaa tcattactct gcctccacta ccatggatta | 960 |
| tcccctctttg gggctgatga ctgagaagct atcccagaaa acatcaatt tgatctttgc | 1020 |
| agtgactgaa aatgtagtca atctctatca gaactatagt gagctcatcc cagggaccac | 1080 |
| agttgggggtt ctgtccatgg attccagcaa tgtcctccag ctcattgttg atgcttatgg | 1140 |
| gaaaatccgt tctaaagtag agctggaagt gcgtgacctc cctgaagagt tgtctctatc | 1200 |
| cttcaatgcc acctgcctca caatgaggt catccctggc ctcaagtctt gtatgggact | 1260 |
| caagattgga gacacggtga gcttcagcat tgaggccaag gtgcgaggct gtccccagga | 1320 |
| gaaggagaag tcctttacca taagcccgt gggcttcaag acagcctga tcgtccaggt | 1380 |
| cacctttgat tgtgactgtg cctgccaggc ccaagctgaa cctaatagcc atcgctgcaa | 1440 |
| caatggcaat gggacctttg agtgtgggt atgccgttgt gggcctggct ggctgggatc | 1500 |
| ccagtgtgag tgctcagagg aggactatcg ccccttcag caggacgaat gcagcccccg | 1560 |
| ggagggtcag cccgtctgca gccagcgggg cgagtgcctc tgtggtcaat gtgtctgcca | 1620 |
| cagcagtgac tttggcaaga tcacgggcaa gtactgcgag tgtgacgact ctcctgtgt | 1680 |

-continued

```
ccgctacaag ggggagatgt gctcaggcca tggccagtgc agctgtgggg actgcctgtg    1740
tgactccgac tggaccggct actactgcaa ctgtaccacg cgtactgaca cctgcatgtc    1800
cagcaatggg ctgctgtgca gcggccgcgg caagtgtgaa tgtggcagct gtgtctgtat    1860
ccagccgggc tcctatgggg acacctgtga gaagtgcccc acctgccag  atgcctgcac    1920
ctttaagaaa gaatgtgtgg agtgtaagaa gtttgaccgg gagccctaca tgaccgaaaa    1980
tacctgcaac cgttactgcc gtgacgagat tgagtcagtg aaagagctta aggacactgg    2040
caaggatgca gtgaattgta cctataagaa tgaggatgca tgtgtcgtca gattccagta    2100
ctatgaagat tctagtggaa agtccatcct gtatgtggta gaagagccag agtgtcccaa    2160
gggccctgac atcctggtgg tcctgctctc agtgatgggg gccattctgc tcattggcct    2220
tgccgccctg ctcatctgga aactcctcat caccatccac gaccgaaaag aattcgctaa    2280
atttgaggaa gaacgcgcca gagcaaaatg ggacacagcc aacaacccac tgtataaaga    2340
ggccacgtct accttcacca atatcacgta ccggggcact taatgataag cagtcatcct    2400
cagatcatta tcagcctgtg ccacgattgc aggagtccct gccatcatgt ttacagagga    2460
cagtatttgt ggggagggat tggggctca  gagtgggta  ggttgggaga atgtcagtat    2520
gtggaagtgt gggtctgtgt gtgtgtatgt ggggtctgt  gtgtttatgt gtgtgtgttg    2580
tgtgtgggag tgtgtaattt aaaattgtga tgtgtcctga taagctgagc tccttagcct    2640
ttgtcccaga atgcctcctg cagggattct tcctgcttag cttgagggtg actatggagc    2700
tgagcaggtg ttcttcatta cctcagtgag aagccagctt tcctcatcag gccattgtcc    2760
ctgaagagaa gggcagggct gaggcctctc attccagagg aagggacacc aagccttggc    2820
tctaccctga gttcataaat ttatggttct caggcctgac tctcagcagc tatggtagga    2880
actgctgggc ttggcagccc gggtcatctg tacctctgcc tcctttcccc tccctcaggc    2940
cgaaggagga gtcagggaga gctgaactat tagagctgcc tgtgcctttt gccatcccct    3000
caacccagct atggttctct cgcaagggaa gtccttgcaa gctaattctt tgacctgttg    3060
ggagtgagga tgtctgggcc actcaggggt cattcatggc ctgggggatg taccagcatc    3120
tcccagttca taatcacaac ccttcagatt tgccttattg gcagctctac tctggaggtt    3180
tgtttagaag aagtgtgtca cccttaggcc agcaccatct ctttacctcc taattccaca    3240
ccctcactgc tgtagacatt tgctatgagc tggggatgtc tctcatgacc aaatgctttt    3300
cctcaaaggg agagagtgct attgtagagc cagaggtctg gccctatgct tccggcctcc    3360
tgtccctcat ccatagcacc tccacatacc tggccctgag ccttggtgtg ctgtatccat    3420
ccatggggct gattgtattt accttctacc tcttggctgc cttgtgaagg aattattccc    3480
atgagttggc tgggaataag tgccaggatg gaatgatggg tcagttgtat cagcacgtgt    3540
ggcctgttct tctatgggtt ggacaacctc attttaactc agtctttaat ctgagaggcc    3600
acagtgcaat tttattttat ttttctcatg atgaggtttt cttaacttaa aagaacatgt    3660
atataaacat gcttgcatta tatttgtaaa tttatgtgta tggcaaagaa ggagagcata    3720
ggaaaccaca cagacttggg cagggtacag acactcccac ttggcatcat tcacagcaag    3780
tcactggcca gtggctggat ctgtgagggg ctctctcatg atagaaggct atggggatag    3840
atgtgtggac acattggacc tttcctgagg aagagggact gttcttttgt cccagaaaag    3900
cagtggctcc attggtgttg acatacatcc aacattaaaa gccaccccca aatgcccaag    3960
aaaaaaagaa agacttatca acatttgttc catgagg                              3997
```

-continued

```
<210> SEQ ID NO 3
<211> LENGTH: 788
<212> TYPE: PRT
<213> ORGANISM: Homo sapiens

<400> SEQUENCE: 3
```

| | | | | | | | | | | | | | | |
|---|---|---|---|---|---|---|---|---|---|---|---|---|---|---|
| Met | Arg | Ala | Arg | Pro | Arg | Pro | Arg | Pro | Leu | Trp | Val | Thr | Val | Leu | Ala |
| 1 | | | | 5 | | | | 10 | | | | 15 | | |
| Leu | Gly | Ala | Leu | Ala | Gly | Val | Gly | Val | Gly | Gly | Pro | Asn | Ile | Cys | Thr |
| | | | 20 | | | | 25 | | | | 30 | | | |
| Thr | Arg | Gly | Val | Ser | Ser | Cys | Gln | Gln | Cys | Leu | Ala | Val | Ser | Pro | Met |
| | | 35 | | | | 40 | | | | 45 | | | | |
| Cys | Ala | Trp | Cys | Ser | Asp | Glu | Ala | Leu | Pro | Leu | Gly | Ser | Pro | Arg | Cys |
| | 50 | | | | | 55 | | | | 60 | | | | |
| Asp | Leu | Lys | Glu | Asn | Leu | Leu | Lys | Asp | Asn | Cys | Ala | Pro | Glu | Ser | Ile |
| 65 | | | | 70 | | | | 75 | | | | 80 | | |
| Glu | Phe | Pro | Val | Ser | Glu | Ala | Arg | Val | Leu | Glu | Asp | Arg | Pro | Leu | Ser |
| | | | 85 | | | | 90 | | | | 95 | | | |
| Asp | Lys | Gly | Ser | Gly | Asp | Ser | Ser | Gln | Val | Thr | Gln | Val | Ser | Pro | Gln |
| | | | 100 | | | | 105 | | | | 110 | | | |
| Arg | Ile | Ala | Leu | Arg | Leu | Arg | Pro | Asp | Asp | Ser | Lys | Asn | Phe | Ser | Ile |
| | | 115 | | | | 120 | | | | 125 | | | | |
| Gln | Val | Arg | Gln | Val | Glu | Asp | Tyr | Pro | Val | Asp | Ile | Tyr | Tyr | Leu | Met |
| 130 | | | | | 135 | | | | 140 | | | | | |
| Asp | Leu | Ser | Tyr | Ser | Met | Lys | Asp | Asp | Leu | Trp | Ser | Ile | Gln | Asn | Leu |
| 145 | | | | 150 | | | | 155 | | | | 160 | | |
| Gly | Thr | Lys | Leu | Ala | Thr | Gln | Met | Arg | Lys | Leu | Thr | Ser | Asn | Leu | Arg |
| | | | 165 | | | | 170 | | | | 175 | | | |
| Ile | Gly | Phe | Gly | Ala | Phe | Val | Asp | Lys | Pro | Val | Ser | Pro | Tyr | Met | Tyr |
| | | | 180 | | | | 185 | | | | 190 | | | |
| Ile | Ser | Pro | Pro | Glu | Ala | Leu | Glu | Asn | Pro | Cys | Tyr | Asp | Met | Lys | Thr |
| | | 195 | | | | 200 | | | | 205 | | | | |
| Thr | Cys | Leu | Pro | Met | Phe | Gly | Tyr | Lys | His | Val | Leu | Thr | Leu | Thr | Asp |
| | 210 | | | | | 215 | | | | 220 | | | | |
| Gln | Val | Thr | Arg | Phe | Asn | Glu | Glu | Val | Lys | Lys | Gln | Ser | Val | Ser | Arg |
| 225 | | | | 230 | | | | 235 | | | | 240 | | |
| Asn | Arg | Asp | Ala | Pro | Glu | Gly | Gly | Phe | Asp | Ala | Ile | Met | Gln | Ala | Thr |
| | | | 245 | | | | 250 | | | | 255 | | | |
| Val | Cys | Asp | Glu | Lys | Ile | Gly | Trp | Arg | Asn | Asp | Ala | Ser | His | Leu | Leu |
| | | | 260 | | | | 265 | | | | 270 | | | |
| Val | Phe | Thr | Thr | Asp | Ala | Lys | Thr | His | Ile | Ala | Leu | Asp | Gly | Arg | Leu |
| | | 275 | | | | 280 | | | | 285 | | | | |
| Ala | Gly | Ile | Val | Gln | Pro | Asn | Asp | Gly | Gln | Cys | His | Val | Gly | Ser | Asp |
| 290 | | | | | 295 | | | | 300 | | | | | |
| Asn | His | Tyr | Ser | Ala | Ser | Thr | Thr | Met | Asp | Tyr | Pro | Ser | Leu | Gly | Leu |
| 305 | | | | 310 | | | | 315 | | | | 320 | | |
| Met | Thr | Glu | Lys | Leu | Ser | Gln | Lys | Asn | Ile | Asn | Leu | Ile | Phe | Ala | Val |
| | | | 325 | | | | 330 | | | | 335 | | | |
| Thr | Glu | Asn | Val | Val | Asn | Leu | Tyr | Gln | Asn | Tyr | Ser | Glu | Leu | Ile | Pro |
| | | | 340 | | | | 345 | | | | 350 | | | |
| Gly | Thr | Thr | Val | Gly | Val | Leu | Ser | Met | Asp | Ser | Ser | Asn | Val | Leu | Gln |
| | | 355 | | | | 360 | | | | 365 | | | | |
| Leu | Ile | Val | Asp | Ala | Tyr | Gly | Lys | Ile | Arg | Ser | Lys | Val | Glu | Leu | Glu |
| 370 | | | | | 375 | | | | 380 | | | | | |

-continued

```
Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
            405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
            435                 440                 445

Asp Ser Leu Ile Val Gln Val Thr Phe Asp Cys Asp Cys Ala Cys Gln
            450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
            485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
            515                 520                 525

Cys Gly Gln Cys Val Cys His Ser Ser Asp Phe Gly Lys Ile Thr Gly
            530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
            565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
            595                 600                 605

Cys Gly Ser Cys Val Cys Ile Gln Pro Gly Ser Tyr Gly Asp Thr Cys
            610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Glu Pro Tyr Met Thr Glu Asn Thr
            645                 650                 655

Cys Asn Arg Tyr Cys Arg Asp Glu Ile Glu Ser Val Lys Glu Leu Lys
            660                 665                 670

Asp Thr Gly Lys Asp Ala Val Asn Cys Thr Tyr Lys Asn Glu Asp Asp
            675                 680                 685

Cys Val Val Arg Phe Gln Tyr Tyr Glu Asp Ser Ser Gly Lys Ser Ile
            690                 695                 700

Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
            725                 730                 735

Ala Leu Leu Ile Trp Lys Leu Leu Ile Thr Ile His Asp Arg Lys Glu
            740                 745                 750

Phe Ala Lys Phe Glu Glu Glu Arg Ala Arg Ala Lys Trp Asp Thr Ala
            755                 760                 765

Asn Asn Pro Leu Tyr Lys Glu Ala Thr Ser Thr Phe Thr Asn Ile Thr
            770                 775                 780

Tyr Arg Gly Thr
785
```

```
<210> SEQ ID NO 4
<211> LENGTH: 788
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|
| Met | Arg | Ala | Arg | Pro | Arg | Pro | Arg | Leu | Trp | Val | Thr | Val | Leu | Ala |
| 1 | | | | 5 | | | | 10 | | | | | 15 | |
| Leu | Gly | Ala | Leu | Ala | Gly | Val | Gly | Val | Gly | Gly | Pro | Asn | Ile | Cys | Thr |
| | | | 20 | | | | | 25 | | | | | 30 | | |
| Thr | Arg | Gly | Val | Ser | Ser | Cys | Gln | Gln | Cys | Leu | Ala | Val | Ser | Pro | Met |
| | | 35 | | | | | 40 | | | | | 45 | | | |
| Cys | Ala | Trp | Cys | Ser | Asp | Glu | Ala | Leu | Pro | Pro | Gly | Ser | Pro | Arg | Cys |
| | 50 | | | | | 55 | | | | | 60 | | | | |
| Asp | Leu | Lys | Glu | Asn | Leu | Leu | Lys | Asp | Asn | Cys | Ala | Pro | Glu | Ser | Ile |
| 65 | | | | | 70 | | | | | 75 | | | | | 80 |
| Glu | Phe | Pro | Val | Ser | Glu | Ala | Arg | Val | Leu | Glu | Asp | Arg | Pro | Leu | Ser |
| | | | | 85 | | | | | 90 | | | | | 95 | |
| Asp | Lys | Gly | Ser | Gly | Asp | Ser | Ser | Gln | Val | Thr | Gln | Val | Ser | Pro | Gln |
| | | | | 100 | | | | | 105 | | | | | 110 | |
| Arg | Ile | Ala | Leu | Arg | Leu | Arg | Pro | Asp | Asp | Ser | Lys | Asn | Phe | Ser | Ile |
| | | | 115 | | | | | 120 | | | | | 125 | | |
| Gln | Val | Arg | Gln | Val | Glu | Asp | Tyr | Pro | Val | Asp | Ile | Tyr | Tyr | Leu | Met |
| | 130 | | | | | 135 | | | | | 140 | | | | |
| Asp | Leu | Ser | Tyr | Ser | Met | Lys | Asp | Asp | Leu | Trp | Ser | Ile | Gln | Asn | Leu |
| 145 | | | | | 150 | | | | | 155 | | | | | 160 |
| Gly | Thr | Lys | Leu | Ala | Thr | Gln | Met | Arg | Lys | Leu | Thr | Ser | Asn | Leu | Arg |
| | | | | 165 | | | | | 170 | | | | | 175 | |
| Ile | Gly | Phe | Gly | Ala | Phe | Val | Asp | Lys | Pro | Val | Ser | Pro | Tyr | Met | Tyr |
| | | | 180 | | | | | 185 | | | | | 190 | | |
| Ile | Ser | Pro | Pro | Glu | Ala | Leu | Glu | Asn | Pro | Cys | Tyr | Asp | Met | Lys | Thr |
| | | 195 | | | | | 200 | | | | | 205 | | | |
| Thr | Cys | Leu | Pro | Met | Phe | Gly | Tyr | Lys | His | Val | Leu | Thr | Leu | Thr | Asp |
| | 210 | | | | | 215 | | | | | 220 | | | | |
| Gln | Val | Thr | Arg | Phe | Asn | Glu | Glu | Val | Lys | Lys | Gln | Ser | Val | Ser | Arg |
| 225 | | | | | 230 | | | | | 235 | | | | | 240 |
| Asn | Arg | Asp | Ala | Pro | Glu | Gly | Gly | Phe | Asp | Ala | Ile | Met | Gln | Ala | Thr |
| | | | | 245 | | | | | 250 | | | | | 255 | |
| Val | Cys | Asp | Glu | Lys | Ile | Gly | Trp | Arg | Asn | Asp | Ala | Ser | His | Leu | Leu |
| | | | 260 | | | | | 265 | | | | | 270 | | |
| Val | Phe | Thr | Thr | Asp | Ala | Lys | Thr | His | Ile | Ala | Leu | Asp | Gly | Arg | Leu |
| | | 275 | | | | | 280 | | | | | 285 | | | |
| Ala | Gly | Ile | Val | Gln | Pro | Asn | Asp | Gly | Gln | Cys | His | Val | Gly | Ser | Asp |
| | 290 | | | | | 295 | | | | | 300 | | | | |
| Asn | His | Tyr | Ser | Ala | Ser | Thr | Thr | Met | Asp | Tyr | Pro | Ser | Leu | Gly | Leu |
| 305 | | | | | 310 | | | | | 315 | | | | | 320 |
| Met | Thr | Glu | Lys | Leu | Ser | Gln | Lys | Asn | Ile | Asn | Leu | Ile | Phe | Ala | Val |
| | | | | 325 | | | | | 330 | | | | | 335 | |
| Thr | Glu | Asn | Val | Val | Asn | Leu | Tyr | Gln | Asn | Tyr | Ser | Glu | Leu | Ile | Pro |
| | | | 340 | | | | | 345 | | | | | 350 | | |
| Gly | Thr | Thr | Val | Gly | Val | Leu | Ser | Met | Asp | Ser | Ser | Asn | Val | Leu | Gln |
| | | 355 | | | | | 360 | | | | | 365 | | | |
| Leu | Ile | Val | Asp | Ala | Tyr | Gly | Lys | Ile | Arg | Ser | Lys | Val | Glu | Leu | Glu |
| | 370 | | | | | 375 | | | | | 380 | | | | |

-continued

```
Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
            405                 410                 415

Ile Gly Asp Thr Val Ser Phe Ser Ile Glu Ala Lys Val Arg Gly Cys
                420                 425                 430

Pro Gln Glu Lys Glu Lys Ser Phe Thr Ile Lys Pro Val Gly Phe Lys
                435                 440                 445

Asp Ser Leu Ile Val Gln Val Thr Phe Asp Cys Asp Cys Ala Cys Gln
            450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
                500                 505                 510

Ser Pro Arg Glu Gly Gln Pro Val Cys Ser Gln Arg Gly Glu Cys Leu
            515                 520                 525

Cys Gly Gln Cys Val Cys His Ser Ser Asp Phe Gly Lys Ile Thr Gly
530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
                580                 585                 590

Cys Met Ser Ser Asn Gly Leu Leu Cys Ser Gly Arg Gly Lys Cys Glu
            595                 600                 605

Cys Gly Ser Cys Val Cys Ile Gln Pro Gly Ser Tyr Gly Asp Thr Cys
            610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Glu Pro Tyr Met Thr Glu Asn Thr
                645                 650                 655

Cys Asn Arg Tyr Cys Arg Asp Glu Ile Glu Ser Val Lys Glu Leu Lys
                660                 665                 670

Asp Thr Gly Lys Asp Ala Val Asn Cys Thr Tyr Lys Asn Glu Asp Asp
                675                 680                 685

Cys Val Val Arg Phe Gln Tyr Tyr Glu Asp Ser Ser Gly Lys Ser Ile
            690                 695                 700

Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
                740                 745                 750

Phe Ala Lys Phe Glu Glu Glu Arg Ala Arg Ala Lys Trp Asp Thr Ala
                755                 760                 765

Asn Asn Pro Leu Tyr Lys Glu Ala Thr Ser Thr Phe Thr Asn Ile Thr
            770                 775                 780

Tyr Arg Gly Thr
785
```

<210> SEQ ID NO 5
<211> LENGTH: 3303
<212> TYPE: DNA
<213> ORGANISM: Homo sapiens

<400> SEQUENCE: 5

| | | | | | |
|---|---|---|---|---|---|
| gatggccaga | gctttgtgtc | cactgcaagc | cctctggctt | ctggagtggg | tgctgctgct | 60 |
| cttgggacct | tgtgctgccc | ctccagcctg | ggccttgaac | ctggacccag | tgcagctcac | 120 |
| cttctatgca | ggccccaatg | gcagccagtt | tggattttca | ctggacttcc | acaaggacag | 180 |
| ccatgggaga | gtgccatcg | tggtgggcgc | ccgcgacc | ctgggcccca | gccaggagga | 240 |
| gacgggcggc | gtgttcctgt | gcccctggag | ggccgagggc | ggccagtgcc | cctcgctgct | 300 |
| ctttgacctc | cgtgatgaga | cccgaaatgt | aggctcccaa | actttacaaa | ccttcaaggc | 360 |
| ccgccaagga | ctggggggcgt | cggtcgtcag | ctggagcgac | gtcattgtgg | cctgcgcccc | 420 |
| ctggcagcac | tggaacgtcc | tagaaaagac | tgaggaggct | gagaagacgc | ccgtaggtag | 480 |
| ctgcttttg | gctcagccag | agagcggccg | ccgcgccgag | tactcccct | gtcgcgggaa | 540 |
| caccctgagc | cgcatttacg | tggaaaatga | ttttagctgg | gacaagcgtt | actgtgaagc | 600 |
| gggcttcagc | tccgtggtca | ctcaggccgg | agagctggtg | cttggggctc | ctggcggcta | 660 |
| ttatttctta | ggtctcctgg | cccaggctcc | agttgcggat | atttctcga | gttaccgccc | 720 |
| aggcatcctt | ttgtggcacg | tgtcctccca | gagcctctcc | tttgactcca | gcaacccaga | 780 |
| gtacttcgac | ggctactggg | ggtactcggt | ggccgtgggc | gagttcgacg | gggatctcaa | 840 |
| cactacagaa | tatgtcgtcg | gtgcccccac | ttggagctgg | accctgggag | cggtggaaat | 900 |
| tttggattcc | tactaccaga | ggctgcatcg | gctgcgcgca | gagcagatgg | cgtcgtattt | 960 |
| tgggcattca | gtggctgtca | ctgacgtcaa | cggggatggg | aggcatgatc | tgctggtggg | 1020 |
| cgctccactg | tatatggaga | gccgggcaga | ccgaaaactg | gccgaagtgg | ggcgtgtgta | 1080 |
| tttgttcctg | cagccgcgag | gcccccacgc | gctgggtgcc | cccagcctcc | tgctgactgg | 1140 |
| cacacagctc | tatgggcgat | tcggctctgc | catcgcaccc | ctgggcgacc | tcaccgggga | 1200 |
| tggctacaat | gacattgcag | tggctgcccc | ctacggggt | cccagtggcc | ggggccaagt | 1260 |
| gctggtgttc | ctgggtcaga | gtgagggggct | gaggtcacgt | ccctcccagg | tcctggacag | 1320 |
| ccccttcccc | acaggctctg | cctttggctt | ctcccttcga | ggtgccgtag | acatcgatga | 1380 |
| caacggatac | ccagacctga | tcgtgggagc | ttacggggcc | aaccaggtgg | ctgtgtacag | 1440 |
| agctcagcca | gtggtgaagg | cctctgtcca | gctactggtg | caagattcac | tgaatcctgc | 1500 |
| tgtgaagagc | tgtgtcctac | ctcagaccaa | gacacccgtg | agctgcttca | acatccagat | 1560 |
| gtgtgttgga | gccactgggc | acaacattcc | tcagaagcta | tccctaaatg | ccgagctgca | 1620 |
| gctggaccgg | cagaagcccc | gccagggccg | gcgggtgctg | ctgctgggct | ctcaacaggc | 1680 |
| aggcaccacc | ctgaacctgg | atctgggcgg | aaagcacagc | cccatctgcc | acaccaccat | 1740 |
| ggccttcctt | cgagatgagg | cagacttccg | ggacaagctg | agcccattg | tgctcagcct | 1800 |
| caatgtgtcc | ctaccgccca | cggaggctgg | aatggcccct | gctgtcgtgc | tgcatggaga | 1860 |
| cacccatgtg | caggagcaga | cacgaatcgt | cctggactct | ggggaagatg | acgtatgtgt | 1920 |
| gccccagctt | cagctcactg | ccagcgtgac | gggctcccg | ctcctagttg | ggcagataa | 1980 |
| tgtcctggag | ctgcagatgg | acgcagccaa | cgagggcgag | ggggcctatg | aagcagagct | 2040 |
| ggccgtgcac | ctgcccagg | gcgcccacta | catgcgggcc | ctaagcaatg | tcgagggctt | 2100 |
| tgagagactc | atctgtaatc | agaagaagga | gaatgagacc | aggtgtgtgc | tgtgtgagct | 2160 |

-continued

```
gggcaacccc atgaagaaga acgcccagat aggaatcgcg atgttggtga gcgtggggaa      2220
tctggaagag gctggggagt ctgtgtcctt ccagctgcag atacggagca agaacagcca      2280
gaatccaaac agcaagattg tgctgctgga cgtgccggtc cgggcagagg cccaagtgga      2340
gctgcgaggg aactcctttc cagcctccct ggtggtggca gcagaagaag gtgagaggga      2400
gcagaacagc ttggacagct ggggacccaa agtggagcac acctatgagc tccacaacaa      2460
tggccctggg actgtgaatg gtcttcacct cagcatccac cttccgggac agtcccagcc      2520
ctccgacctg ctctacatcc tggatataca gccccagggg ggccttcagt gcttcccaca      2580
gcctcctgtc aaccctctca aggtggactg ggggctgccc atccccagcc cctcccccat      2640
tcacccggcc catcacaagc gggatcgcag acagatcttc ctgccagagc ccgagcagcc      2700
ctcgaggctt caggatccag ttctcgtaag ctgcgactcg gcgccctgta ctgtggtgca      2760
gtgtgacctg caggagatgg cgcgcgggca gcgggccatg gtcacggtgc tggccttcct      2820
gtggctgccc agcctctacc agaggcctct ggatcagttt gtgctgcagt cgcacgcatg      2880
gttcaacgtg tcctccctcc cctatgcggt gccccgctc agcctgcccc gagggaagc      2940
tcaggtgtgg acacagctgc tccgggcctt ggaggagagg gccattccaa tctggtgggt      3000
gctggtgggt gtgctgggtg gcctgctgct gctcaccatc ctggtcctgg ccatgtggaa      3060
ggtcggcttc ttcaagcgga accggccacc cctggaagaa gatgatgaag aggggagtg      3120
atggtgcagc ctacactatt ctagcaggag ggttgggcgt gctacctgca ccgccccttc      3180
tccaacaagt tgcctccaag cttttgggttg gagctgttcc attgggtcct cttggtgtcg      3240
tttccctccc aacagagctg ggctacccccc cctcctgctg cctaataaag agactgagcc      3300
ctg                                                                    3303

<210> SEQ ID NO 6
<211> LENGTH: 3303
<212> TYPE: DNA
<213> ORGANISM: Homo sapiens

<400> SEQUENCE: 6
gatggccaga gctttgtgtc cactgcaagc cctctggctt ctggagtggg tgctgctgct       60
cttgggacct tgtgctgccc ctccagcctg ggccttgaac ctggacccag tgcagctcac      120
cttctatgca ggccccaatg gcagccagtt tggattttca ctggacttcc acaaggacag      180
ccatgggaga gtggccatcg tggtgggcgc ccgcggaccc tgggccccca gcaggagga      240
gacgggcggc gtgttcctgt gcccctggag ggccgagggc ggccagtgcc cctcgctgct      300
ctttgacctc cgtgatgaga cccgaaatgt aggctcccaa actttacaaa ccttcaaggc      360
ccgccaagga ctggggcgt cggtcgtcag ctggagcgac gtcattgtgg cctgcgcccc      420
ctggcagcac tggaacgtcc tagaaaagac tgaggaggct gagaagacgc ccgtaggtag      480
ctgcttttg gctcagccag agagcggccg ccgcgccgag tactcccct gtcgcgggaa      540
caccctgagc cgcatttacg tggaaaatga ttttagctgg acaagcgtt actgtgaagc      600
gggcttcagc tccgtggtca ctcaggccgg agagctggtc cttggggctc ctggcggcta      660
ttatttctta ggtctcctgg cccaggctcc agttgcggat attttctcga gttaccgccc      720
aggcatcctt tgtggcacg tgtcctccca gagcctctcc tttgactcca gcaacccaga      780
gtacttcgac ggctactggg ggtactcggt ggccgtgggc gagttcgacg ggatctcaa      840
cactacagaa tatgtcgtcg gtgccccac ttggagctga accctgggag cggtggaaat      900
tttggattcc tactaccaga ggctgcatcg gctgcgcgca gagcagatgg cgtcgtatt      960
```

-continued

```
tgggcattca gtggctgtca ctgacgtcaa cggggatggg aggcatgatc tgctggtggg    1020
cgctccactg tatatggaga gccgggcaga ccgaaaactg gccgaagtgg ggcgtgtgta    1080
tttgttcctg cagccgcgag gcccccacgc gctgggtgcc cccagcctcc tgctgactgg    1140
cacacagctc tatgggcgat tcggctctgc catcgcaccc ctgggcgacc tcgaccggga    1200
tggctacaat gacattgcag tggctgcccc ctacgggggt cccagtggcc ggggccaagt    1260
gctggtgttc ctgggtcaga gtgaggggct gaggtcacgt ccctcccagg tcctggacag    1320
cccccttccc acaggctctg cctttggctt ctcccttcga ggtgccgtag acatcgatga    1380
caacggatac ccagacctga tcgtgggagc ttacggggcc aaccaggtgg ctgtgtacag    1440
agctcagcca gtggtgaagg cctctgtcca gctactggtg caagattcac tgaatcctgc    1500
tgtgaagagc tgtgtcctac ctcagaccaa gacacccgtg agctgcttca acatccagat    1560
gtgtgttgga gccactgggc acaacattcc tcagaagcta tccctaaatg ccgagctgca    1620
gctggaccgg cagaagcccc gccagggccg gcgggtgctg ctgctgggct ctcaacaggc    1680
aggcaccacc ctgaacctgg atctgggcgg aaagcacagc cccatctgcc acaccaccat    1740
ggccttcctt cgagatgagg cagacttccg ggacaagctg agccccattg tgctcagcct    1800
caatgtgtcc ctaccgccca cggaggctgg aatggcccct gctgtcgtgc tgcatggaga    1860
cacccatgtg caggagcaga cacgaatcgt cctggactct ggggaagatg acgtatgtgt    1920
gccccagctt cagctcactg ccagcgtgac gggctcccg ctcctagttg ggcagataa     1980 tgtcctggag ctgcagatgg acgcagccaa cgagggcgag ggggcctatg aagcagagct    2040
ggccgtgcac ctgccccagg gcgcccacta catgcgggcc taagcaatg tcgagggctt     2100 tgagagactc atctgtaatc agaagaagga gaatgagacc agggtggtgc tgtgtgagct    2160
gggcaacccc atgaagaaga acgcccagat aggaatcgcg atgttggtga gcgtggggaa    2220
tctggaagag gctggggagt ctgtgtcctt ccagctgcag atacggagca agaacagcca    2280
gaatccaaac agcaagattg tgctgctgga cgtgccggtc cgggcagagg cccaagtgga    2340
gctgcgaggg aactcctttc cagcctccct ggtggtggca gcagaagaag gtgagaggga    2400
gcagaacagc ttggacagct ggggacccaa agtggagcac acctatgagc tccacaacaa    2460
tggccctggg actgtgaatg gtcttcacct cagcatccac cttccgggac agtcccagcc    2520
ctccgacctg ctctacatcc tggatataca gccccagggg ggccttcagt gcttcccaca    2580
gcctcctgtc aaccctctca aggtggactg ggggctgccc agcccagcc cctcccccat     2640 tcacccggcc catcacaagc gggatcgcag acagatcttc ctgccagagc ccgagcagcc    2700
ctcgaggctt caggatccag ttctcgtaag ctgcgactcg gcgccctgta ctgtggtgca    2760
gtgtgacctg caggagatgg cgcgcgggca gcgggccatg gtcacggtgc tggccttcct    2820
gtggctgccc agcctctacc agaggcctct ggatcagttt gtgctgcagt cgcacgcatg    2880
gttcaacgtg tcctccctcc cctatgcggt gccccgctc agcctgcccc gagggggaagc    2940 tcaggtgtgg acacagctgc tccgggcctt ggaggagagg gccattccaa tctggtgggt    3000
gctggtgggt gtgctgggtg gcctgctgct gctcaccatc ctggtcctgg ccatgtggaa    3060
ggtcggcttc ttcaagcgga accggccacc cctggaagaa gatgatgaag aggggagtg     3120 atggtgcagc ctacactatt ctagcaggag ggttgggcgt gctacctgca ccgccccttc    3180
tccaacaagt tgcctccaag cttgggttg gagctgttcc attgggtcct cttggtgtcg      3240
tttccctccc aacagagctg ggctacccccc cctcctgctg cctaataaag agactgagcc    3300
``` ctg                                                                    3303

<210> SEQ ID NO 7
<211> LENGTH: 1039
<212> TYPE: PRT
<213> ORGANISM: Homo sapiens

<400> SEQUENCE: 7

Met Ala Arg Ala Leu Cys Pro Leu Gln Ala Leu Trp Leu Leu Glu Trp
1               5                   10                  15

Val Leu Leu Leu Gly Pro Cys Ala Ala Pro Pro Ala Trp Ala Leu
            20                  25                  30

Asn Leu Asp Pro Val Gln Leu Thr Phe Tyr Ala Gly Pro Asn Gly Ser
            35                  40                  45

Gln Phe Gly Phe Ser Leu Asp Phe His Lys Asp Ser His Gly Arg Val
    50                  55                  60

Ala Ile Val Val Gly Ala Pro Arg Thr Leu Gly Pro Ser Gln Glu Glu
65                  70                  75                  80

Thr Gly Gly Val Phe Leu Cys Pro Trp Arg Ala Glu Gly Gly Gln Cys
                85                  90                  95

Pro Ser Leu Leu Phe Asp Leu Arg Asp Glu Thr Arg Asn Val Gly Ser
                100                 105                 110

Gln Thr Leu Gln Thr Phe Lys Ala Arg Gln Gly Leu Gly Ala Ser Val
            115                 120                 125

Val Ser Trp Ser Asp Val Ile Val Ala Cys Ala Pro Trp Gln His Trp
            130                 135                 140

Asn Val Leu Glu Lys Thr Glu Glu Ala Glu Lys Thr Pro Val Gly Ser
145                 150                 155                 160

Cys Phe Leu Ala Gln Pro Glu Ser Gly Arg Arg Ala Glu Tyr Ser Pro
                165                 170                 175

Cys Arg Gly Asn Thr Leu Ser Arg Ile Tyr Val Glu Asn Asp Phe Ser
            180                 185                 190

Trp Asp Lys Arg Tyr Cys Glu Ala Gly Phe Ser Ser Val Val Thr Gln
            195                 200                 205

Ala Gly Glu Leu Val Leu Gly Ala Pro Gly Gly Tyr Tyr Phe Leu Gly
    210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Ser Gln Ser Leu Ser Phe Asp Ser
                245                 250                 255

Ser Asn Pro Glu Tyr Phe Asp Gly Tyr Trp Gly Tyr Ser Val Ala Val
                260                 265                 270

Gly Glu Phe Asp Gly Asp Leu Asn Thr Thr Glu Tyr Val Val Gly Ala
            275                 280                 285

Pro Thr Trp Ser Trp Thr Leu Gly Ala Val Glu Ile Leu Asp Ser Tyr
    290                 295                 300

Tyr Gln Arg Leu His Arg Leu Arg Ala Glu Gln Met Ala Ser Tyr Phe
305                 310                 315                 320

Gly His Ser Val Ala Val Thr Asp Val Asn Gly Asp Gly Arg His Asp
                325                 330                 335

Leu Leu Val Gly Ala Pro Leu Tyr Met Glu Ser Arg Ala Asp Arg Lys
            340                 345                 350

Leu Ala Glu Val Gly Arg Val Tyr Leu Phe Leu Gln Pro Arg Gly Pro
            355                 360                 365

```
His Ala Leu Gly Ala Pro Ser Leu Leu Leu Thr Gly Thr Gln Leu Tyr
    370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Pro Ser Gly
                405                 410                 415

Arg Gly Gln Val Leu Val Phe Leu Gly Gln Ser Glu Gly Leu Arg Ser
            420                 425                 430

Arg Pro Ser Gln Val Leu Asp Ser Pro Phe Pro Thr Gly Ser Ala Phe
            435                 440                 445

Gly Phe Ser Leu Arg Gly Ala Val Asp Ile Asp Asp Asn Gly Tyr Pro
450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
            500                 505                 510

Val Ser Cys Phe Asn Ile Gln Met Cys Val Gly Ala Thr Gly His Asn
            515                 520                 525

Ile Pro Gln Lys Leu Ser Leu Asn Ala Glu Leu Gln Leu Asp Arg Gln
    530                 535                 540

Lys Pro Arg Gln Gly Arg Arg Val Leu Leu Leu Gly Ser Gln Gln Ala
545                 550                 555                 560

Gly Thr Thr Leu Asn Leu Asp Leu Gly Gly Lys His Ser Pro Ile Cys
                565                 570                 575

His Thr Thr Met Ala Phe Leu Arg Asp Glu Ala Asp Phe Arg Asp Lys
            580                 585                 590

Leu Ser Pro Ile Val Leu Ser Leu Asn Val Ser Leu Pro Pro Thr Glu
            595                 600                 605

Ala Gly Met Ala Pro Ala Val Val Leu His Gly Asp Thr His Val Gln
610                 615                 620

Glu Gln Thr Arg Ile Val Leu Asp Ser Gly Glu Asp Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
            660                 665                 670

Glu Gly Ala Tyr Glu Ala Glu Leu Ala Val His Leu Pro Gln Gly Ala
            675                 680                 685

His Tyr Met Arg Ala Leu Ser Asn Val Glu Gly Phe Glu Arg Leu Ile
    690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750

Gln Ile Arg Ser Lys Asn Ser Gln Asn Pro Asn Ser Lys Ile Val Leu
            755                 760                 765

Leu Asp Val Pro Val Arg Ala Glu Ala Gln Val Glu Leu Arg Gly Asn
770                 775                 780

Ser Phe Pro Ala Ser Leu Val Val Ala Ala Glu Glu Gly Glu Arg Glu
```

```
                785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
                820                 825                 830

His Leu Pro Gly Gln Ser Gln Pro Ser Asp Leu Leu Tyr Ile Leu Asp
                835                 840                 845

Ile Gln Pro Gln Gly Gly Leu Gln Cys Phe Pro Gln Pro Pro Val Asn
        850                 855                 860

Pro Leu Lys Val Asp Trp Gly Leu Pro Ile Pro Ser Pro Ser Pro Ile
865                 870                 875                 880

His Pro Ala His His Lys Arg Asp Arg Arg Gln Ile Phe Leu Pro Glu
                885                 890                 895

Pro Glu Gln Pro Ser Arg Leu Gln Asp Pro Val Leu Val Ser Cys Asp
                900                 905                 910

Ser Ala Pro Cys Thr Val Val Gln Cys Asp Leu Gln Glu Met Ala Arg
        915                 920                 925

Gly Gln Arg Ala Met Val Thr Val Leu Ala Phe Leu Trp Leu Pro Ser
    930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
                980                 985                 990

Arg Ala Ile Pro Ile Trp Trp Val Leu Val Gly Val Leu Gly Gly Leu
        995                 1000                1005

Leu Leu Leu Thr Ile Leu Val Leu Ala Met Trp Lys Val Gly Phe Phe
    1010                1015                1020

Lys Arg Asn Arg Pro Pro Leu Glu Glu Asp Asp Glu Glu Gly Glu
1025                1030                1035

<210> SEQ ID NO 8
<211> LENGTH: 1039
<212> TYPE: PRT
<213> ORGANISM: Homo sapiens

<400> SEQUENCE: 8

Met Ala Arg Ala Leu Cys Pro Leu Gln Ala Leu Trp Leu Leu Glu Trp
1               5                   10                  15

Val Leu Leu Leu Leu Gly Pro Cys Ala Ala Pro Pro Ala Trp Ala Leu
                20                  25                  30

Asn Leu Asp Pro Val Gln Leu Thr Phe Tyr Ala Gly Pro Asn Gly Ser
            35                  40                  45

Gln Phe Gly Phe Ser Leu Asp Phe His Lys Asp Ser His Gly Arg Val
        50                  55                  60

Ala Ile Val Val Gly Ala Pro Arg Thr Leu Gly Pro Ser Gln Glu Glu
65                  70                  75                  80

Thr Gly Gly Val Phe Leu Cys Pro Trp Arg Ala Glu Gly Gly Gln Cys
                85                  90                  95

Pro Ser Leu Leu Phe Asp Leu Arg Asp Glu Thr Arg Asn Val Gly Ser
            100                 105                 110

Gln Thr Leu Gln Thr Phe Lys Ala Arg Gln Gly Leu Gly Ala Ser Val
        115                 120                 125
```

-continued

```
Val Ser Trp Ser Asp Val Ile Val Ala Cys Ala Pro Trp Gln His Trp
    130                 135                 140

Asn Val Leu Glu Lys Thr Glu Ala Glu Lys Thr Pro Val Gly Ser
145                 150                 155                 160

Cys Phe Leu Ala Gln Pro Glu Ser Gly Arg Arg Ala Glu Tyr Ser Pro
                165                 170                 175

Cys Arg Gly Asn Thr Leu Ser Arg Ile Tyr Val Glu Asn Asp Phe Ser
                180                 185                 190

Trp Asp Lys Arg Tyr Cys Glu Ala Gly Phe Ser Ser Val Val Thr Gln
            195                 200                 205

Ala Gly Glu Leu Val Leu Gly Ala Pro Gly Gly Tyr Tyr Phe Leu Gly
    210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Ser Gln Ser Leu Ser Phe Asp Ser
                245                 250                 255

Ser Asn Pro Glu Tyr Phe Asp Gly Tyr Trp Gly Tyr Ser Val Ala Val
                260                 265                 270

Gly Glu Phe Asp Gly Asp Leu Asn Thr Thr Glu Tyr Val Val Gly Ala
            275                 280                 285

Pro Thr Trp Ser Trp Thr Leu Gly Ala Val Glu Ile Leu Asp Ser Tyr
    290                 295                 300

Tyr Gln Arg Leu His Arg Leu Arg Ala Glu Gln Met Ala Ser Tyr Phe
305                 310                 315                 320

Gly His Ser Val Ala Val Thr Asp Val Asn Gly Asp Gly Arg His Asp
                325                 330                 335

Leu Leu Val Gly Ala Pro Leu Tyr Met Glu Ser Arg Ala Asp Arg Lys
                340                 345                 350

Leu Ala Glu Val Gly Arg Val Tyr Leu Phe Leu Gln Pro Arg Gly Pro
            355                 360                 365

His Ala Leu Gly Ala Pro Ser Leu Leu Leu Thr Gly Thr Gln Leu Tyr
    370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                405                 410                 415

Arg Gly Gln Val Leu Val Phe Leu Gly Gln Ser Glu Gly Leu Arg Ser
                420                 425                 430

Arg Pro Ser Gln Val Leu Asp Ser Pro Phe Pro Thr Gly Ser Ala Phe
            435                 440                 445

Gly Phe Ser Leu Arg Gly Ala Val Asp Ile Asp Asp Asn Gly Tyr Pro
    450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
                500                 505                 510

Val Ser Cys Phe Asn Ile Gln Met Cys Val Gly Ala Thr Gly His Asn
            515                 520                 525

Ile Pro Gln Lys Leu Ser Leu Asn Ala Glu Leu Gln Leu Asp Arg Gln
    530                 535                 540

Lys Pro Arg Gln Gly Arg Arg Val Leu Leu Leu Gly Ser Gln Gln Ala
```

```
                                      -continued
545                 550                 555                 560

Gly Thr Thr Leu Asn Leu Asp Leu Gly Gly Lys His Ser Pro Ile Cys
                565                 570                 575

His Thr Thr Met Ala Phe Leu Arg Asp Glu Ala Asp Phe Arg Asp Lys
                580                 585                 590

Leu Ser Pro Ile Val Leu Ser Leu Asn Val Ser Leu Pro Pro Thr Glu
                595                 600                 605

Ala Gly Met Ala Pro Ala Val Val Leu His Gly Asp Thr His Val Gln
                610                 615                 620

Glu Gln Thr Arg Ile Val Leu Asp Ser Gly Glu Asp Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
                660                 665                 670

Glu Gly Ala Tyr Glu Ala Glu Leu Ala Val His Leu Pro Gln Gly Ala
                675                 680                 685

His Tyr Met Arg Ala Leu Ser Asn Val Glu Gly Phe Glu Arg Leu Ile
                690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
                740                 745                 750

Gln Ile Arg Ser Lys Asn Ser Gln Asn Pro Asn Ser Lys Ile Val Leu
                755                 760                 765

Leu Asp Val Pro Val Arg Ala Glu Ala Gln Val Glu Leu Arg Gly Asn
                770                 775                 780

Ser Phe Pro Ala Ser Leu Val Val Ala Ala Glu Gly Glu Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
                820                 825                 830

His Leu Pro Gly Gln Ser Gln Pro Ser Asp Leu Leu Tyr Ile Leu Asp
                835                 840                 845

Ile Gln Pro Gln Gly Gly Leu Gln Cys Phe Pro Gln Pro Pro Val Asn
850                 855                 860

Pro Leu Lys Val Asp Trp Gly Leu Pro Ser Pro Ser Pro Ser Pro Ile
865                 870                 875                 880

His Pro Ala His His Lys Arg Asp Arg Arg Gln Ile Phe Leu Pro Glu
                885                 890                 895

Pro Glu Gln Pro Ser Arg Leu Gln Asp Pro Val Leu Val Ser Cys Asp
                900                 905                 910

Ser Ala Pro Cys Thr Val Val Gln Cys Asp Leu Gln Glu Met Ala Arg
                915                 920                 925

Gly Gln Arg Ala Met Val Thr Val Leu Ala Phe Leu Trp Leu Pro Ser
                930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975
```

```
Arg Gly Glu Ala Gln Val Trp Thr Gln Leu Leu Arg Ala Leu Glu Glu
        980                 985                 990

Arg Ala Ile Pro Ile Trp Trp Val Leu Val Gly Val Leu Gly Gly Leu
        995                 1000                1005

Leu Leu Leu Thr Ile Leu Val Leu Ala Met Trp Lys Val Gly Phe Phe
    1010                1015                1020

Lys Arg Asn Arg Pro Pro Leu Glu Glu Asp Asp Glu Glu Gly Glu
1025                1030                1035

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
agacttcctc ctcagacctc cacct                                    25

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
taaactctta gctattggga agtggta                                  27

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ttctgattgc tggacttctc tt                                       22

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
tctctcccca tggcaaagag t                                        21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ctgtcaaccc tctcaaggta a                                        21

<210> SEQ ID NO 14
<211> LENGTH: 27
<212> TYPE: DNA
<213> ORGANISM: Artificial Sequence
<220> FEATURE:
```

-continued

<223> OTHER INFORMATION: Synthetic

<400> SEQUENCE: 14
gccgggtgaa tgggggaggg gctggcg     27

METHODS FOR TREATING OR IDENTIFYING A SUBJECT AT RISK FOR A NEUROLOGICAL DISEASE BY DETERMINING THE PRESENCE OF A VARIANT GPIIIA AND/OR VARIANT BPIIB ALLELE

CROSS REFERENCE TO RELATED APPLICATIONS

This application claims priority to U.S. Provisional Application Ser. No. 60/102,624, filed on Oct. 1, 1998.

BACKGROUND OF THE INVENTION

In general, the invention relates to methods for treating a neurological disease.

Neurological diseases, for example, Alzheimer's disease, are often difficult to diagnose and occur in the population in a manner which is difficult to predict. A method that would allow one to identify subjects having a neurological disease, or being at risk for developing a neurological disease, would allow for the more timely administration of an appropriate therapy.

The GPIIIa gene encodes a 788 amino acid polypeptide with a 26-residue signal peptide, a 29-residue transmembrane domain near the carboxy terminus, and four cysteine-rich domains of 33–38 residues each (Zimrin et al., *J Clin. Invest.* 81:1470–1475 (1988)). Two different antigenic forms of GPIIIa, alloantigens PlA1 and PlA2 (for Platelet Antigen 1 and 2), have been described and can be distinguished using a monoclonal antibody (Weiss et al., *Tissue Antigens* 46:374–381 (1995)). The most predominant form of GPIIIa, PlA1, is carried by 98% of the Caucasian population. The rarer form of GPIIIa, PlA2, has sustained a point mutation at base 192 that causes a nucleotide change from a T to a C and thus a leucine to proline (CTG>CCG) amino acid substitution at residue position 33 (Newman et al., *J. Clin. Invest.* 83:1778–1781 (1989)).

The GPIIb polypeptide is the larger component of the GPIIIa/GPIIb complex and comprises two disulfide-linked subunits of 137 amino acids and 871 amino acids each. The larger GPIIb polypeptide has a 26 amino acid signal sequence, a potential transmembrane domain, and four stretches of 12 amino acids each that are homologous to the calcium binding sites of calmodulin and troponin C (Poncz et al., *J Biol. Chem.* 262(18):8476–8482 (1987)). Mutational analysis of these domains has indicated that these calcium-binding domains are required for the correct folding and transport of the GPIIb polypeptide to the cell surface (Basani et al., *Blood* 88:167–173 (1996)). Two antigenic forms of GPIIb, Bak$^a$ and Bak$^b$, have been described and can be distinguished using specific antisera. The less common form of GPIIb (i.e., Bak$^b$) was determined to have a T to G point mutation that results in an isoleucine to serine substitution at amino acid position 843 (Lyman et al., *Blood* 75:2343–2348 (1990)).

SUMMARY OF THE INVENTION

The present invention provides methods for identifying or treating a subject at risk for, or diagnosed with, a neurological disease.

In the first aspect, the invention provides a method for identifying a subject at risk for a neurological disease by: identifying the subject; determining the genotype or phenotype of the GPIIIa or GPIIb locus of the subject; and determining the presence of a variant GPIIIa or variant GPIIb allele or isoform, where the presence of the variant GPIIIa allele or isoform or the variant GPIIb allele or isoform is indicative of the subject having an increased risk of the neurological disease. Preferably, the neurological disease is Alzheimer's Disease (AD).

In the second aspect, the invention provides a method for diagnosing a subject with a neurological disease by: identifying the subject; determining the genotype or phenotype of the GPIIIa or GPIIb locus of the subject; and determining the presence of a variant GPIIIa or a variant GPIIb allele or isoform, where the presence of the variant GPIIIa allele or isoform or the variant GPIIb allele or isoform is indicative of the subject having a likelihood of the neurological disease.

In the third aspect, the invention provides a method for characterizing the genotype of at least one subject involved in a clinical trial of a therapy for the treatment of a neurological disease by: identifying the subject; determining the genotype or phenotype of the GPIIIa or GPIIb locus of the subject before, during, or after the clinical trial; and determining the presence of a variant GPIIIa or a variant GPIIb allele or isoform, where the presence of the variant GPIIIa allele or isoform or the variant GPIIb allele or isoform places the subject into a subgroup for the clinical trial. Preferably, the genotype or phenotype is indexed against the efficacy or side-effects of the therapy.

In the fourth aspect, the invention provides a method for treating a subject with a neurological disease by: identifying the subject; determining the genotype or phenotype of the GPIIIa or GPIIb locus of the subject; determining the presence of a variant GPIIIa or a variant GPIIb allele or isoform; and determining the preferred therapy for the treatment of the neurological disease.

In the fifth aspect, the invention provides a method for treating a subject at risk for a neurological disease by: identifying the subject; determining the genotype or phenotype of the GPIIIa or GPIIb locus of the subject; determining the presence of a variant GPIIIa or a variant GPIIb allele or isoform; determining the GPIIIa or GPIIb allele status of the subject, where the allele status is predictive of patient outcome or drug efficacy.

In a preferred embodiment of the above aspects, the method includes determining the presence of both the variant GPIIIa allele or isoform and the variant GPIIb allele or isoform.

In other preferred embodiments of the above aspects, the neurological disease may be Alzheimer's disease (AD), a non-AD neurological disease, or a neurological disease selected from the group consisting of Alzheimer's disease, neurofibromatosis, Huntington's disease, depression, amyotrophic lateral sclerosis, multiple sclerosis, stroke, Parkinson's disease, and multi-infarct dementia.

In other preferred embodiments of the above aspects, the determining may be performed using a nucleic acid that specifically binds a nucleic acid encoded by the variant GPIIIa allele or the variant GPIIb allele. In other preferred embodiments of the above aspects, the determining may be performed using an antibody that specifically binds a polypeptide encoded by the variant GPIIIa allele or the variant GPIIb allele, but does not bind a polypeptide encoded by a wild-type GPIIIa allele or a wild-type GPIIb allele.

In other preferred embodiments of the above aspects, the variant GPIIIa allele may have a point mutation at nucleotide base 192 of SEQ ID NO: 2 or encode a polypeptide with a proline at amino acid position 33 of SEQ ID NO: 4.

In other preferred embodiments of the above aspects, the variant GPIIb allele may have a point mutation at nucleotide base 2622 of SEQ ID NO: 6 or encode a polypeptide with a serine at amino acid position 843 of SEQ ID NO: 8.

The presence of a variant allele may be determined by genotyping nucleic acids from the subject or by assaying for the presence of a protein having alterations encoded by the variant nucleic acid.

By "neurological disease" is meant a disease, which involves the neuronal cells of the nervous system. Specifically included are: prion diseases (e.g, Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, tyrosinemia, and fragile X syndrome); pathologies of the mature brain (e.g., neurofibromatosis, Huntington's disease, depression, amyotrophic lateral sclerosis, multiple sclerosis); conditions that strike in adulthood (e.g. Alzheimer's disease, Creutzfeldt-Jakob disease, Lewy body disease, Parkinson's disease, Pick's disease); and other pathologies of the brain (e.g., brain mishaps, brain injury, coma, infections by various agents, dietary deficiencies, stroke, multiple infarct dementia, and cardiovascular accidents).

By "cognitive enhancers" is meant drugs which enhance a) memory performance, whether it is verbal memory, spatial memory, or factual memory and b) learning capacity.

By "cholinomimetic therapy" is meant any drug that mimics the function of acetylcholine or enhances the activity of acetylcholine synthesizing cells. These drugs include, but are not limited to, inhibitors of acetylcholine degradation (acetylcholine esterase inhibitors such as tacrine), drugs that mimic acetylcholine structure and function, drugs that block acetylcholine uptake by neurons, and drugs that interact with pre-synaptic receptors to induce acetylcholine release from cholinergic neurons.

By "non-cholinomimetic vasopressinergic therapy" is meant a therapy that utilizes a vasopressinergic modulator such as, for example, S12024 (provided by Servier, Les Laboratoires Servier, 22 rue Garnier, 92200 Neuilly sur Seine, France).

By "already diagnosed" is meant already diagnosed as having the neurological disease, having a genetic predisposition to the disease, or both.

By "patient profile" is meant data pertaining to the patient for whom the pharmacogenetic analysis is being performed. Data may include information on the patient's diagnosis, age, sex, and genotype. The patient's profile may also include materials from the patient such as blood or purified RNA or DNA.

By "prognosis protocol" is meant a therapy plan provided to the clinician or patient using the pharmacogenetic method. The prognosis protocol includes an indication of whether or not the patient is likely to respond positively to a cholinomimetic therapeutic. In preferred embodiments, the protocol also includes an indication of the drug dose to which the patient is most likely to respond. The "pharmacogenetic method" is a method whereby genetic and diagnostic data, including the patient's neurological diagnosis and the patient's GPIIIa and/or GPIIb genotype are processed to provide therapeutic options and prognoses.

By "non-AD neurological disease" is meant a disease other than Alzheimer's disease, which involves the neuronal cells of the nervous system. Specifically included are: prion diseases (e.g, Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, tyrosinemia, and fragile X syndrome); pathologies of the mature brain (e.g., neurofibromatosis, Huntington's disease, depression, amyotrophic lateral sclerosis, multiple sclerosis); conditions that strike in adulthood (e.g. Creutzfeldt-Jakob disease, Lewy body disease, Parkinson's disease, Pick's disease); and other pathologies of the brain (e.g., brain mishaps, brain injury, coma, infections by various agents, dietary deficiencies, stroke, multi-infarct dementia, and cardiovascular accidents).

By "Alzheimer's Disease" is meant a pathology characterized by an early and extensive loss of entorhinal cortex neurons. Alzheimer's disease subjects may be identified by progressive and degenerative effects on the brain which are not attributable to other causes. A diagnosis of Alzheimer's disease is made using clinical-neuropathological correlations known in the art (see e.g., *Arch. Neurology* 51(9): 888–896 (1994)). Post-mortem, the disease may be diagnosed by the presence of amyloid plaques and fibrils.

As used herein, by "therapy for the treatment of a neurological disease" is meant any therapy suitable for treating a neurological disease. A suitable therapy can be a pharmacological agent or drug that may enhance or slow the loss of cognitive function, motor function, or neuronal activity of the central nervous system, peripheral nervous system, or inhibit the further deterioration of any of these faculties. In addition, the term therapy may also include the close monitoring of an asymptomatic patient for the appearance of any symptoms of a neurological disease.

By "determining the presence of a variant GPIIIa and/or variant GPIIb allele" is meant subjecting a nucleic acid sample to any of a variety of detection techniques known in the art for elucidating a point mutation in a nucleic acid (e.g., polymerase chain reaction (PCR), reverse transcriptase-PCR (RT-PCR), ligase-mediated chain reaction step, chip hybridization methods, or restriction enzyme-mediated digestion). For example, in the presence of appropriately designed primers, a nucleic acid fragment can be amplified using PCR and analyzed by restriction enzyme digestion that can reveal the presence of a variant allelic sequence. In addition, DNA sequencing may be employed using techniques known in the art. These nucleic acid techniques allow for a genotype determination of the GPIIIa or GPIIb locus. Alternatively, phenotyping of the locus may be performed (and a genotype thus inferred) by using standard techniques for detecting the presence of a polypeptide having a particular amino acid change (e.g., antibodies, isoelectric focusing, and 2-D PAGE). For example, the presence of a variant GPIIIa polypeptide (e.g., PlA2; LEU33PRO) can be distinguished from a wild-type GPIIIa polypeptide (i.e., PlA1) using epitope specific antibodies available in the art (Weiss et al., *Tissue Antigens* 46:374–381 (1995)). Antibodies for detecting different polymorphisms of the GPIIb polypeptide have also been described (Lyman et al., *Blood* 75:2343–2348 (1990)).

By "variant GPIIIa allele" is meant any sequence mutation of the glycoprotein integrin beta-3 subunit (GPIIIa) gene, that differs from the predominant wild-type allelic sequence (e.g., variant GPIIIa allele (LEU33PRO)) and which is associated with neurological disease. By "associated" is meant associated with an altered risk of disease incidence, drug efficacy, or disease prognosis. Variant GPIIIa alleles not specifically described to be associated with neurological disease herein can be tested for association using the techniques provided herein and those known in the art. Specifically excluded are GPIIIa variants that have an A>C mutation at nucleotide base 1159, and A>G mutation at nucleotide base 1549, or a G>C mutation at nucleotide base 1161.

By "variant GPIIb allele" is meant any sequence mutation of the glycoprotein integrin alpha-2 subunit (GPIIb) gene that differs from the predominant wild-type allelic sequence (e.g., variant GPIIb allele (ILE843SER)) and which is associated with neurological disease. By "associated" is meant associated with an altered risk of disease incidence, drug efficacy, or disease prognosis. Variant GPIIb alleles not specifically described to be associated with neurological disease herein can be tested for association using the techniques provided herein and those known in the art. Specifically excluded are GPIIIa variants that have an A>C mutation at nucleotide base 1159, and A>G mutation at nucleotide base 1549, or a G>C mutation at nucleotide base 1161.

By "risk factor associated with a disease" is meant any risk factor for a disease known in the art. Examples of risk factors commonly associated with diseases include age, gender, diet, exercise, weight, the presence of another disease, and the occurrence of a specific genotype. Risk factors associated with a neurological disease in particular may include advanced age, lower intelligence, smaller head size, history of head trauma, mutations on chromosomes 1, 14, and 21, or the presence of a variant GPIIIa and/or variant GPIIb allele (see e.g., Cummings et al., *Neurology* (1 Supp.1):S2-S17, 1998).

By "subject at risk for a neurological disease" is meant a subject identified or diagnosed as having a neurological disease or having a genetic predisposition or risk for acquiring a neurological disease using the methods of the invention and techniques available to those skilled in the art.

By "wild-type" is meant any allele, or polypeptide encoded by such an allele, that is present in that part of the population considered free of disease.

By "PCR, RT-PCR, or ligase chain reaction amplification" is meant subjecting a DNA sample to a Polymerase Chain Reaction step or ligase-mediated chain reaction step, or RNA to a RT-PCR step, such that, in the presence of appropriately designed primers, a nucleic acid fragment is synthesized or fails to be synthesized, thereby revealing the allele status of a patient. The nucleic acid may be further analyzed by DNA sequencing using techniques known in the art.

The present invention provides a number of advantages. For example, the methods described herein allow for a determination of a subject's GPIIIa and/or GPIIb genotype for the timely administration of a prophylactic therapy for the treatment of a neurological disease.

Other features and advantages of the invention will be apparent from the following detailed description and from the claims.

DETAILED DESCRIPTION OF THE INVENTION

The drawings will first be described.

BRIEF DESCRIPTION OF THE DRAWINGS

FIG. 1 is a depiction of the cDNA sequence encoding the wild type human GPIIIa polypeptide (SEQ ID NO: 1).

FIG. 2 is a depiction of the cDNA sequence encoding the variant human GPIIIa polypeptide (SEQ ID NO: 2) which has a nucleotide point mutation at base 192. The T to C point mutation creates a new Msp I restriction site (underlined) and results in a codon that encodes a proline at position 33 (indicated in bold and offset by spaces).

FIG. 3 is a depiction of the amino acid sequence of the wild type human GPIIIa polypeptide (SEQ ID NO: 3). The 26 amino acid signal sequence is underlined and the wild type leucine residue at position 33 is indicated in bold.

FIG. 4 is a depiction of the amino acid sequence of the human GPIIIa polypeptide (SEQ ID NO: 4) with a single amino acid residue change, from an leucine (L) to a proline (P) at position 33, indicated in bold. The 26 amino acid signal sequence is underlined.

FIG. 5 is a depiction of the cDNA sequence encoding the wild-type human GPIIB polypeptide (SEQ ID NO: 5). The codon encoding the wild-type isoleucine residue at position 843 is indicated in bold.

FIG. 6 represents the cDNA sequence encoding the variant human glycoprotein IIb polypeptide (SEQ ID NO: 6) which has a point mutation (T to G) at nucleotide base 2622. The point mutation creates a new Hae II restriction site (underlined) and a codon (indicated in bold and offset by spaces) that encodes a serine at position 843.

FIG. 7 shows the amino acid sequence of the wild-type human glycoprotein IIb polypeptide (SEQ ID NO: 7). The wild-type isoleucine residue at position 843 is indicated in bold.

FIG. 8 shows the amino acid sequence of the variant human glycoprotein IIb polypeptide (SEQ ID NO: 8). The single amino acid residue change, from an isoleucine (I) to a serine (S) at position 843, is indicated in bold.

The invention described herein features methods for treating or identifying a subject at risk for a neurological disease, such as Alzheimer's disease (AD), by determining the presence of a variant GPIIIa or variant GPIIb allele. The invention also provides a method for forecasting patient outcome and the suitability of the patient for entering a clinical drug trial for the testing of a therapy for a neurological disease.

Normally, these alleles encode glycoproteins IIIa and IIb of the GPIIIa/GPIIb complex that belongs to a class of multi-subunit integrin receptors that bind cell adhesion molecules. These receptors are composed of alpha and beta subunits referred to, counter intuitively, as GPIIb and GPIIIa, respectively. Together, the GPIIIa beta and GPIIb alpha subunits form part of the platelet complex receptor, fibronectin receptor, and vitronectin receptor, and play a role in clotting. As expected, these polypeptides are expressed in platelets and endothelial cells (Hynes et al., *Cell* 48: 549–554 (1987)).

We have discovered that GPIIb and GPIIIa alleles are associated with the occurrence of neurological disease. For example, the presence of a particular variant GPIIIa allele that results in a single amino acid change from a leucine to a proline at residue 33 (LEU33PRO) indicates, with a high probability, that a subject is at risk for a neurological disease such as Alzheimer's disease (AD). In addition, we have also observed that the presence of a variant GPIIb allele (ILE843SER) indicates, with a similar probability, that a subject may be at risk for acquiring a neurological disease, such as AD. Importantly, these genes may act in synergy and when used together as a prognostic tool, predict, with even greater probability, a subject's risk for a neurological disease, such as AD.

One of the advantages of the invention is that a subject at risk for a neurological disease may be identified and, if appropriate, administered therapeutics without waiting for debilitating symptoms of them required for definitive diagnosis to occur. Initially, treatment of a subject having a variant allele described herein may involve monitoring of the subject for other risk factors and/or symptoms. Alternatively, a subject at high risk for a neurological disease may be treated prophylactically, with therapies known in the art, in order to delay, inhibit, or prevent the onset of disease. In one approach, the presence of a variant GPIIIa and/or variant GPIIb allele is rapidly determined using a sensitive PCR assay and, alone or in combination with a determination of other risk factors associated with a neurological disease, this determination is used to determine if a prophylactic treatment therapy should be invoked.

The prediction of drug efficacy may involve cholinomimetic therapies, for example, tacrine, or non-cholinomimetic therapies, for example, a vasopressinergic drug. The invention provides a treatment protocol that utilizes one of the following therapies for a neurological disease: probucol, a monoamine oxidase inhibitor, muscarinic agonist, neurotrophic factor, noradrenergic factor, antioxidant, anti-inflammatory, corticotrophin-releasing hormone (CRH), somatostatin, substance P, neuropeptide Y, or thyrotrophin-releasing hormone (TRH).

The findings described herein indicate the predictive value of a variant GPIIIa and/or variant GPIIb allele in treating patients at risk for a neurological disease, such as Alzheimer's disease (AD). In addition, because the underlying mechanism influenced by the variant GPIIIa and/or variant GPIIb allele status is not disease-specific, the GPIIIa and/or GPIIb allele-status is suitable for making patient predictions for non-AD neurological diseases as well.

The following examples, which describe preferred techniques and experimental results, are provided for the purpose of illustrating the invention, and should not be construed as limiting.

EXAMPLE 1

Methods for Determining the Presence of a Variant GPIIIa Allele or Variant GPIIb Allele We have found that both the variant GPIIIa allele and GPIIb allele have strong predictive value for identifying a subject at risk for a neurological disease (e.g., Alzheimer's disease). This predictive value is even stronger when these variant alleles in both genes occur together in a given subject. To demonstrate the effectiveness of the variant GPIIIa and/or variant GPIIb allele for identifying subjects with such a disease risk, we determined the allele frequency of either variant allele in a large number of subjects diagnosed with Alzheimer's disease (N=136) as compared to age-matched healthy controls (N=70).
GPIIIa Genotyping We genotyped each of the above patients for the presence of a variant GPIIIa allele using the polymerase chain reaction method (PCR). In particular, genotyping was carried out by subjecting nucleic acid samples encoding the GPIIIa gene to a polymerase chain reaction (PCR) amplification step followed by another round of PCR amplification using a nested PCR protocol. The first round of PCR amplification was conducted using outside primers PlA2-4 (5'-AGA CTT CCT CCT CAG ACC TCC ACC T-3' (SEQ ID NO: 9)) and PlA2-5 (5'-TAA ACT CTT AGC TAT TGG GAA GTG GTA-3' (SEQ ID NO: 10)) and using reaction conditions that included a heating step at 90° C. for 1 min., followed by another heating step at 95° C. for 1 min., followed by 45 cycles of 94° C. for 25 sec., 45° C. for 55 sec., 72° C. for 45 sec., and a final extension step at 72° C. for 3 min. Next, a 1 µl aliquot of the first PCR reaction was used for conducting the subsequent nested PCR reaction under the same conditions except that the amplification step performed at 45° C. was changed to 48° C. and the oligonucleotides PlA2-1 (5'-TTC TGA TTG CTG GAC TTC TCT T-3' (SEQ ID NO: 11))and PlA2-2(5'-TCT CTC CCC ATG GCA AAG AGT-3' (SEQ ID NO: 12)) were used.

When amplified GPIIIa DNA isolated from the subjects described above was analyzed, we observed a C nucleotide at base position 192 only in nucleic acids encoded by the variant GPIIIa allele (or PlA2 form) and this created a new Msp I restriction site (see FIGS. 1 and 2). Subsequent restriction enzyme analysis of nucleic acids generated by PCR showed that Msp I digestion permitted clear discrimination between the type (PlA1) and mutant form (PlA2) of GPIIIa and individuals could thus be genotyped.

Specifically, a 5 µl aliquot of the resultant amplified PCR reaction product was digested with 5 units of the restriction enzyme Msp I and the resultant DNA products were analyzed using agarose gel electrophoresis and visualized by ethidium bromide staining. Another Msp I site, common to both wild-type and variant GPIIIa alleles, was used as an internal control to insure the completion of Msp I digestion. Using this protocol, three banding patterns were observed based on whether the subject was homozygous wild-type (T/T), heterozygous mutant (C/T), or homozygous mutant (C/C) for the variant GPIIIa allele (LEU33PRO). The banding pattern for the homozygous wild-type consisted of two DNA fragments of 222 bp and 38 bp in length. The banding pattern for the homozygous mutant genotype consisted of three fragments of 175 bp, 49 bp, and 38 bp in length. Accordingly, the banding pattern for the heterozygous mutant genotype consisted of four fragments of 224 bp, 175 bp, 49 bp, and 38 bp in length. A GPIIIa genotype (LEU33PRO) was determined for each subject in the study and analyzed for its predictive value (Examples 2 and 3).
GPIIb Genotyping Each of the above the samples from the patients described above were genotyped for the presence of a variant GPIIb allele using the conditions above with the following modifications. Genotyping was carried out using the same PCR conditions above except that primers A (5'-CTG TCA ACC CTC TCA AGG TAA (SEQ ID NO: 13)) and B (5'-GCC GGG TGA ATG GGG GAG GGG CTG GCG (SEQ ID NO:14)) were used.

Following the PCR amplification reaction, DNA products were digested with the restriction enzyme Hae II (according to the manufacturer) and resultant products were resolved using 3% Nusieve™ gel electrophoresis followed by ethidium bromide staining. As the variant GPIIb nucleic acid encodes an additional Hae II site, distinctive banding patterns were observed based on whether the subject was wild-type (T/T; 180 bp only), heterozygous mutant (C/T; 180, 155, and 25 bp), or homozygous mutant (C/C; 155 and 25 bp) for the GPIIb allele (ILE843SER).
GPIIIa and GPIIB Phenotyping For either the GPIIIa (LEU33PRO) or GPIIb (ILE843SER) gene product, detection of the variant polypeptide may be performed (and a genotype thus inferred) using variant polypeptide specific antibodies as described in the art (see, e.g., Weiss et al., *Tissue Antigens* 46:374–381 (1995); Lyman et al., *Blood* 75:2343–2348 (1990)).

In addition to the above-mentioned methods, the methods provided in U.S. Pat. Nos. 5,935,781; and 6,022,683 any of the pending applications (Ser. Nos. US97/22699, 09/140, 462, now U.S. Pat. No. 6,066,041 Ser. No. 08/991,850, now U.S. Pat. No. 6,251,587, Ser. No. 09/334,489, and 09/616, 506 pending and following references (Brindle N. et al., *Hum. Mol. Genet.* 7:933–935 (1998); Singleton et al., *Hum Mol Genet* 7:937–939 (1998); Lehmann et al., *Hum. Mol. Genet.* 6:1933–1936 (1997); Richard et al., *Lancet* 349:539

(1997); and Gustincich S, et al., *Biotechniques* 11(3) :298–300 (1998)) may also be used.

EXAMPLE 2

Use of the Variant GPIIIa Allele in Determining a Subjects's Risk for Alzheimer's Disease We have discovered that the presence of a variant GPIIIa allele (LEU33PRO) contributes an individual's risk for the development of Alzheimer's disease. To reach this conclusion, we compiled the GPIIIa genotypes for 135 Alzheimer's disease subjects and 69 age-matched healthy controls (Table 1) and analyzed the distribution of variant GPIIIa alleles in control subjects versus subjects with disease. As shown in Table 1, a significant number of subjects diagnosed with Alzheimer's disease had at least one mutant GPIIIa allele.

TABLE 1

GPIIIa Nucleotide Dimorphism in Controls vs. Subjects with Alzheimer's Disease (AD)

| Genotype | C/C (homozygous mt) | C/T (heterozygous mt) | T/T (wild-type) |
|---|---|---|---|
| Control | 1 | 13 | 55 |
| AD | 2 | 46 | 87 |

In Table 2 we present the total number of subjects having at least one variant GPIIIa allele as a function of the subject's disease status. This data shows that the occurrence of a variant GPIIIa allele in a subject with Alzheimer's disease is more than twice as high as in age-matched healthy controls (the odds ratio (O.R.) is 2.17). The Yates value calculated for this data set indicates that this distribution occurring by chance alone is remote (4%). These data predict a strong correlation between the presence of the variant GPIIIa allele and the occurrence of Alzheimer's disease in a given subject.

TABLE 2

Chi Square for GPIIIa Allelic Frequency in Controls vs. Subjects with Alzheimer's Disease (AD)

| | AD | Control |
|---|---|---|
| C/C or C/T (Mutant Genotypes) | 48 | 14 |
| T/T (Wild-Type Genotype) | 87 | 55 |

Yates = 0.037
O.R. = 2.17

In Table 3 the data is shown as the total number of mutant alleles (a C at base position 192) versus wild-type alleles (a T at position 192) occurring in subjects of each health group (i.e., control vs. AD). Stated in another way, each mutant allele is counted and a frequency of occurrence (ranging from 0–1.0) is calculated for the likely appearance of this allele in either a healthy subject or a subject with Alzheimer's disease. A percent occurrence is obtained by multiplying the frequency factor by 100. Thus, the frequency of the variant GPIIIa allele occurring in subjects diagnosed with Alzheimer's disease was 18.5 % (0.185×100) as compared to only 11% in healthy age-matched controls.

TABLE 3

Variant GPIIIa Allele Frequency in Controls vs. Subjects with Alzheimer's Disease (AD)

| | C (Mutant Alleles) | T (Wild-Type Alleles) |
|---|---|---|
| Control | 0.11 (15/138) | 0.89 (123/138) |
| AD | 0.185 (50/270) | 0.815 (220/270) |

Finally, as shown in Tables 4–9, we examined a number of silent mutations (i.e., a wild-type protein is encoded from a mutated nucleic acid) found within the coding region of the GPIIIa gene and found no correlation (the odds ratios are all around 1) between AD and the presence of these mutations. These studies indicate that it is likely that the GPIIIa polypeptide, and not the nucleic acid, plays a possible role in AD. Accordingly, nucleic acid changes that result in amino acid alterations are more likely to be predictive of neurological disease or a predisposition to neurological disease.

TABLE 4

Val 381 Val Silent Mutation (A-C at base 1159) Genotype of Normal Subjects vs. Patients with AD

| | AA wild-type | AC heterozygous mt | CC homozygous mt |
|---|---|---|---|
| Alzheimer's cases | 51 | 62 | 23 |
| Control | 26 | 35 | 9 |

TABLE 5

Odds Ratio and Chi-Square Analysis of the Val 381 Val Silent Mutation Occurring in Patients with AD as Compared to Controls

| | AD | Control |
|---|---|---|
| CX | 85 | 44 |
| AA | 51 | 26 |

Chi-square = 0.92
O.R. = 0.98

TABLE 6

Glu 511 Glu Silent Mutation (A-G at base 1549) Genotype of Normal Subjects vs. Patients with AD

| | AA wild-type | AG heterozygous mutant | GG homozygous mt |
|---|---|---|---|
| Alzheimer's cases | 0 | 36 | 33 |
| Control | 0 | 66 | 69 |

TABLE 7

Odds Ratio and Chi-Square Analysis of the Glu 511 Glu Silent Mutation Occurring in Patients with AD as Compared to Controls

| | AD | Control |
|---|---|---|
| CX | 66 | 36 |
| AA | 69 | 33 |

Chi-square = 0.76
O.R. = 0.88

TABLE 8

Arg 515 Arg Silent Mutation (G-C at base 1161) Genotype of Normal Subjects vs. Patients with AD

|  | AA wild-type | AG heterozygous mt | GG homozygous mt |
|---|---|---|---|
| Alzheimer's cases | 5 | 28 | 34 |
| Control | 19 | 50 | 64 |

TABLE 9

Odds Ratio and Chi-Square Analysis of the Arg 515 Arg Silent Mutation Occurring in Patients with AD as Compared to Controls

|  | AD | Control |
|---|---|---|
| CX | 69 | 33 |
| AA | 64 | 34 |

Chi-square = 0.84
O.R. = 1.11

EXAMPLE 3

Use of the Variant GPIIb Allele Alone and in Combination with the Variant GPIIIa Allele in Determining a Subject's Risk for Alzheimer's Disease Using the techniques presented in Example 1, we determined the GPIIb genotype of patients with AD and normal control subjects (Table 10).

TABLE 10

Variant GPIIb Genotype in Normal Subjects vs. Patients with AD

| Genotype | GG (homozygous mt.) | GT (heterozygous mt.) | TT (wild-type) |
|---|---|---|---|
| Alzheimer's Cases | 15 | 71 | 50 |
| Control | 8 | 28 | 34 |

We observed that a significant number of subjects with AD had at least one mutant GPIIb allele. A chi-square and odds ratio analysis was performed on this data set (Table 11). A significative increase in the odds ratio (p value of 0.10) was seen in patients with AD as compared to age-matched healthy control subjects. This supports the notion that the GPIIb gene may be involved in the development of neurological disease such as AD.

TABLE 11

Odds Ratio and Chi-Square Analysis of the GPIIb Allele Occurring in Normal Subjects vs. Patients with AD CX versus TT

| Genotypes | Alzheimer's Cases | Control |
|---|---|---|
| GX (mutant genotypes) | 86 | 36 |
| TT (wild-type) | 50 | 34 |

O.R. = 1.62 (C.I. 0.91 to 2.91)
Chi-square p = 0.10

Given these findings we decided to explore the possibility that the predictive value of the variant GPIIIa allele and the variant GPIIb allele could be used together in predicting a neurological disease risk. The occurrence of these alleles appearing individually or together in normal subjects versus patients with AD is presented below

TABLE 12

GPIIIa (Leu33Pro)/GPIIb (Ile843Ser) Genotypes in Normal Subjects vs. Patients with AD

| GPIIIa (L33P) | GPIIb (I843S) | Control | AD | O.R. | P value |
|---|---|---|---|---|---|
| − | − | 27 | 34 | Ref | — |
| − | + | 29 | 53 | 1.45 | 0.28 |
| + | − | 7 | 16 | 1.82 | 0.25 |
| + | + | 7 | 33 | 3.74 | 0.005 |

Importantly, we found that in addition to the GPIIIa or GPIIb variant alleles being present at high levels in patients with AD (with an odds ratio of 1.82 and 1.45, respectively), together these alleles were present at an even higher level (with an odds ratio of 3.74). Stated another way, patients with AD are almost 4-fold more likely to have mutations in both the GPIIIa and GPIIb allele than normal control subjects. Thus, we have determined that there is an added predictive value or synergy in using both of these alleles when evaluating a subject for a neurological disease risk.

EXAMPLE 4

Use of the Variant GPIIIa and GPIIb Alleles for Prognosis in Alzheimer's Disease We believe that the method of the invention can be used as a powerful prognostic tool for the treatment of Alzheimer's disease. For example, subjects can be tested at an early asymptomatic age for the presence of a variant GPIIIa and/or GPIIb allele and administered an appropriate prophylactic therapy. Initially, for asymptomatic subjects, this may involve a characterization of other risk factors associated with Alzheimer's disease, avoidance of environmental risk factors, and/or close monitoring. Accordingly, a subject may be characterized as a candidate for prophylactic therapies that can delay, inhibit, or prevent degenerative neurological symptoms. Further, either alone or in combination with other health data, the variant GPIIIa and GPIIb alleles can be used to predict a subject's outcome by comparing the subjects GPIIIa and GPIIb genotypes (and other health data) to a patient database containing the GPIIIa and GPIIb genotypes (and other health data) of similarly afflicted subjects. Based on this database comparison, a subject's likely outcome, i.e., progression of disease, cure rate, response to therapy, morbidity and mortality, can be statistically assessed.

Thus, our results demonstrate that the presence of the variant GPIIIa and/or GPIIb alleles can afford subjects at risk for a neurological disease (e.g., Alzheimer's disease) the ability to start prophylactic therapies before disease strikes. Ideally, the risk of Alzheimer's disease is calculated for all individuals when they are asymptomatic, young adults and well before the onset of measurable symptoms. Then preventive therapies are invoked, as the individual ages, in order to stop or lessen the progression of Alzheimer's disease later in life.

Other Embodiments

The invention described herein provides a method for treating subjects with a neurological disease risk by determining a subject's GPIIIa and/or GPIIb genotype and providing an appropriate therapy based on that determination. We believe that the predictive value of these alleles may also include other variant GPIIIa or GPIIb alleles associated with a neurological disease (e.g., Alzheimer's disease) and this may be readily determined using the methods of the invention. For example, any other variant GPIIIa allele may be detected using the methods described in Example 1. Known polymorphisms in GPIIIa that may be determined to be variants using the methods of the invention are: GPIIIa (ARG62Term), GPIIIa (LEU117TRP), GPIIIa (ASP119TYR), GPIIIa (SER162LEU), GPIIIa (ARG214GLN), GPIIIa (ARG214TRP), GPIIIa (CYS374TYR), GPIIIa (PRO407ALA), GPIIIa (ARG636CYS), and GPIIIA(SER752PRO). Using the guidance provided in Example 2, one can calculate the allelic frequency of the variant GPIIIa allele/s in patients diagnosed with Alzheimer's disease, as compared to healthy control subjects, and determine if the particular variant GPIIIa allele is over represented in patients with disease. Likewise, known polymorphisms in GPIIb may also be exploited, alone, or in combination with the above GPIIIa mutations. GPIIb variants which may be tested are: GPIIb (LEU183PRO), GPIIb (GLY242ASP), GPIIb (PHE289SER), GPIIb (GLU324LYS), GPIIb (ARG327HIS), GPIIb (GLY418ASP), GPIIb (ARG553TERM), GPIIb (ILE565THR), GPIIb (GLN747PRO), and GPIIb (SER870TERM). Furthermore, the predictive value of these alleles can then be assessed and, if appropriate, used alone or in combination with other risk factors for the treatment of Alzheimer's disease.

In addition, while the methods described herein are preferably used for the treatment of human subjects. Non-human animals (e.g., pets and livestock) may also be treated using the methods of the invention.

All publications and patent applications mentioned in this specification are herein incorporated by reference to the same extent as if each independent publication or patent application was specifically and individually indicated to be incorporated by reference.

Other embodiments are within the claims.

What is claimed is:

1. A method for identifying a subject at risk for Alzheimer's disease comprising determining the genotype at nucleotide 192 of the GPIIIa gene of SEQ ID NO.: 2, wherein the mutation encodes a polypeptide with a proline at amino acid position 33 of SEQ ID NO.: 4, and/or at nucleotide 2622 of GPIIb of gene of SEQ ID NO.: 6, wherein the mutation encodes a polypeptide with a serine at amino acid position 843 of SEQ ID NO.: 8, of said subject, wherein said genotype is indicative of said subject having an increased risk for Alzheimer's disease.

2. A method for diagnosing a subject with Alzheimer's disease comprising determining the genotype at nucleotide 192 of the GPIIIa gene of SEQ ID NO.: 2, wherein the mutation encodes a polypeptide with a proline at amino acid position 33 of SEQ ID NO.: 4, and/or at nucleotide 2622 of the GPIIb gene of SEQ ID NO.: 6, wherein the mutation encodes a polypeptide with a serine at amino acid position 843 of SEQ ID NO.: 8, of said subject, wherein said genotype is indicative of said subject having Alzheimer's disease.

3. A method for characterizing the genotype of at least one subject involved in a clinical trial of a therapy for the treatment of Alzheimer's disease comprising determining the genotype at nucleotide 192 of the GPIIIa gene of SEQ ID NO.: 2, wherein the mutation encodes a polypeptide with a proline at amino acid position 33 of SEQ ID NO.: 4, and/or at nucleotide 2622 of the GPIIb gene of SEQ ID NO.: 6, wherein the mutation encodes a polypeptide with a serine at amino acid position 843 of SEQ ID NO.: 8, of said subject.

4. The method of claim 1, 2, or 3, wherein said method comprises determining said genotype at nucleotide 192 of the GPIIIa gene and at nucleotide 2622 of the GPIIb gene of said subject and said genotype places said subject into a subgroup for said clinical trial.

5. The method of claim 1, 2, or 3, wherein said determining is performed using a nucleic acid molecule that specifically binds a GPIIIa nucleic acid molecule.

6. The method of claim 1, 2, or 3, wherein said determining is performed using a nucleic acid molecule that specifically binds a GPIIb nucleic acid molecule.

7. The method of claim 1, 2, or 3, wherein said genotype is T/C at nucleotide 192 of SEQ ID NO: 2.

8. The method of claim 1, 2, or 3, wherein said genotype is T/G at nucleotide 2622 of SEQ ID NO: 6.

9. The method of claim 1, 2, or 3, wherein said GPIIIa gene encodes a polypeptide with a proline at amino acid position 33 of SEQ ID NO: 4.

10. The method of claim 1, 2, or 3, wherein said GPIIb gene encodes a polypeptide with a serine at amino acid position 843 of SEQ ID NO: 8.

11. The method of claim 3, wherein said genotype is indicative of the efficacy or therapeutic benefits of said therapy.

12. The method of claim 1, 2, or 3, wherein said determining the genotype at nucleotide 192 of the GPIIIa gene comprises performing restriction enzyme digestion of an amplified product of a GPIIIa nucleic acid molecule using the enzyme MspI.

13. The method of claim 12, wherein said amplified product is a polymerase chain reaction product and said GPIIIa nucleic acid molecule is a GPIIIA gene or a GPIIIa cDNA.

14. The method of claim 1, 2, or 3, wherein said determining the genotype at nucleotide 2622 of the GPIIb gene comprises performing restriction enzyme digestion of an amplified product of a GPIIb nucleic acid molecule using the enzyme HaeII.

15. The method of claim 14, wherein said amplified product is a polymerase chain reaction product and said GPIIb nucleic acid molecule is a GPIIb gene or a GPIIb cDNA.

* * * * *

UNITED STATES PATENT AND TRADEMARK OFFICE
CERTIFICATE OF CORRECTION

PATENT NO.      : 6,368,797 B1
DATED           : April 9, 2002
INVENTOR(S)     : Keith Schappert It is certified that error appears in the above-identified patent and that said Letters Patent is hereby corrected as shown below:

Title page,
Item [56], OTHER PUBLICATIONS, within the Gustincich et al. reference title, replace "Boold," with -- Blood, --;
Within the Noguchi et al. reference title, replace "Alsheimer's" with -- Alzheimer's --;
Within the Payami et al. reference title, replace "Alsheimer's" with -- Alzheimer's --;

Column 1,
Line 5, within the title, replace "BPIIB" with -- GPIIB --;

Column 6,
Line 15, replace "GPIIB" with -- GPIIb --;

Column 8,
Line 60, replace "6,022,683" with -- U.S. Pat. No. 6,022,683 --;

Column 12,
Line 4, replace "below" with -- below (Table 12). --; and

Column 48,
Line 34, replace "GPIIIA gene" with -- GPIIIa gene --.

Signed and Sealed this

Eleventh Day of February, 2003

JAMES E. ROGAN
*Director of the United States Patent and Trademark Office*